(12) United States Patent  
Shturman et al.

(10) Patent No.: US 7,507,245 B2  
(45) Date of Patent: Mar. 24, 2009

(54) ROTATIONAL ANGIOPLASTY DEVICE WITH ABRASIVE CROWN

(75) Inventors: Leonid Shturman, Greenwich, CT (US); Dmitrii Urjevich Proudnikov, Schelkovskoe shosse (RU); Aleksi Filippovich Filippov, Borovskoe shosse (RU); Arkadiy Smagin, Moscow (RU)

(73) Assignee: Cardiovascular Systems, Inc., St. Paul, MN (US)

( * ) Notice: Subject to any disclaimer, the term of this patent is extended or adjusted under 35 U.S.C. 154(b) by 350 days.

(21) Appl. No.: 10/272,164

(22) Filed: Oct. 16, 2002

(65) Prior Publication Data

US 2003/0125756 A1 Jul. 3, 2003

(51) Int. Cl.
*A61B 17/00* (2006.01)

(52) U.S. Cl. ...................................... 606/159

(58) Field of Classification Search .............. 606/159, 606/170, 171, 174, 180, 1; 604/22
See application file for complete search history.

(56) References Cited

U.S. PATENT DOCUMENTS 5,584,843 A * 12/1996 Wulfman et al. ............ 606/159
5,897,566 A * 4/1999 Shturman et al. ........... 606/159
6,132,444 A * 10/2000 Shturman et al. ........... 606/159

* cited by examiner

*Primary Examiner*—Kevin T Truong
(74) *Attorney, Agent, or Firm*—Altera Law Group, LLC; Jeffrey R. Stone

(57) ABSTRACT

A rotational angioplasty device comprising a flexible, elongated drive shaft rotatable about an axis of rotation of the drive shaft, the drive shaft comprising one or more helically wound wires and having an eccentric enlarged diameter section and an abrasive crown mounted on the enlarged diameter section of the drive shaft.

21 Claims, 36 Drawing Sheets

| ABRASIVE SLEEVE OR CROWN | | | | | | DRIVE SHAFT | | | | |
|---|---|---|---|---|---|---|---|---|---|---|
| 22D (mm) | 92D (mm) | 52D (mm) | 52E (mm) | L (mm) | α | Maximum Diameter of enlarged diameter section (mm) | Length of enlarged diameter section (mm) | Diameters of distal portion 1035 and distal section 1036 before etching (mm) | Diameter of distal portion 1035 after etching (mm) | Diameter of distal section 1036 after etching (mm) |
| 1.07 | 0.92-0.01 | 0.82-0.01 | 0.78+0.01 | 0.9-0.05 | 30° | 0.81 | 3.71 | 0.672 | 0.632 | 0.640 |
| 1.25 | 1.13-0.01 | 1.03-0.01 | 0.9+0.01 | 0.9-0.05 | 30° | 1.04 | 3.68 | 0.672 | 0.632 | 0.640 |
| 1.70 | 1.56-0.01 | 1.46-0.01 | 1.42+0.01 | 1.1-0.05 | 30° | 1.46 | 6.35 | 0.672 | 0.632 | 0.640 |
| 1.93 | 1.80-0.01 | 1.70-0.01 | 1.64+0.01 | 1.5-0.05 | 30° | 1.63 | 10.3 | 0.672 | 0.632 | 0.640 |

Fig 9B

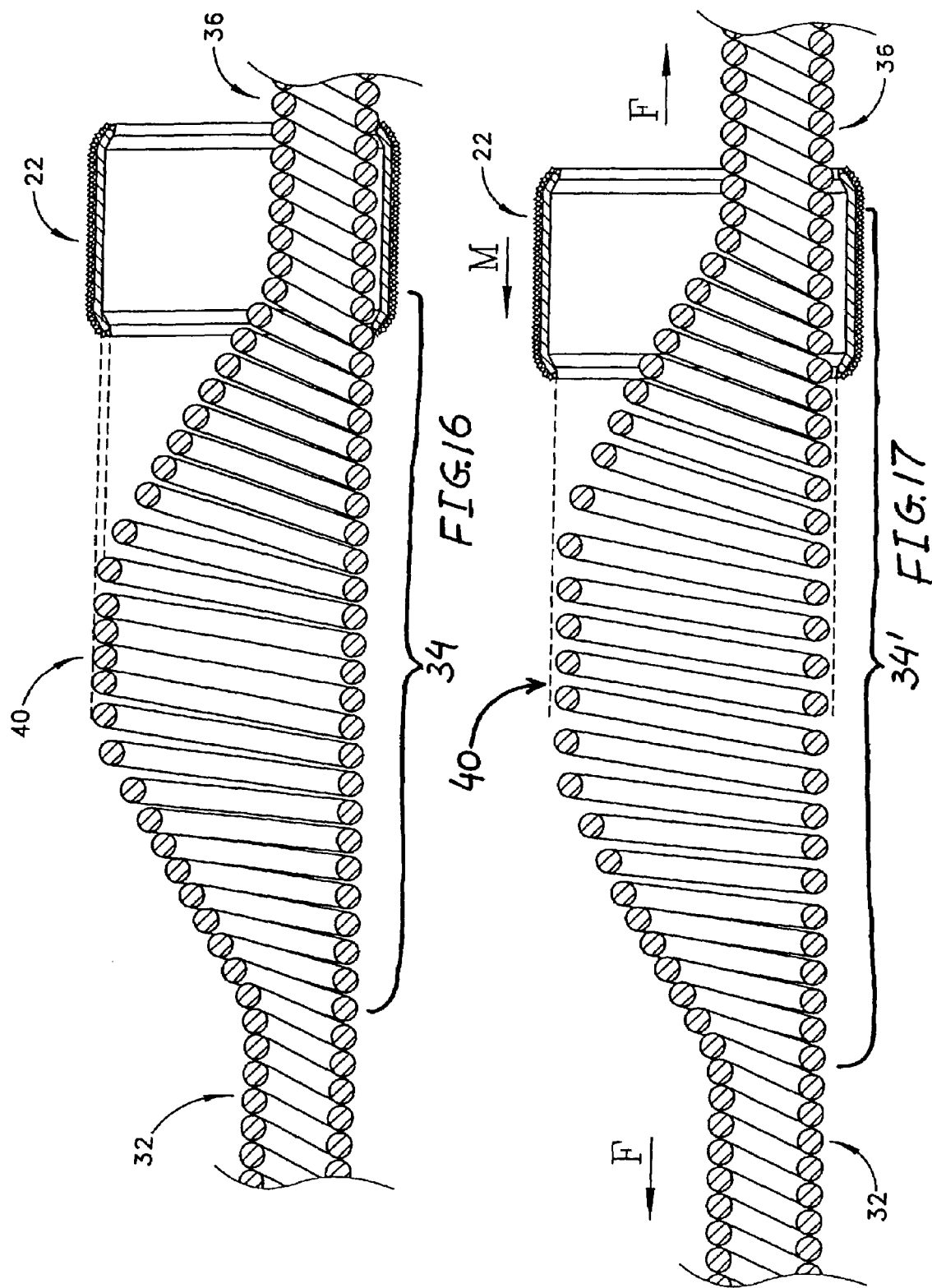

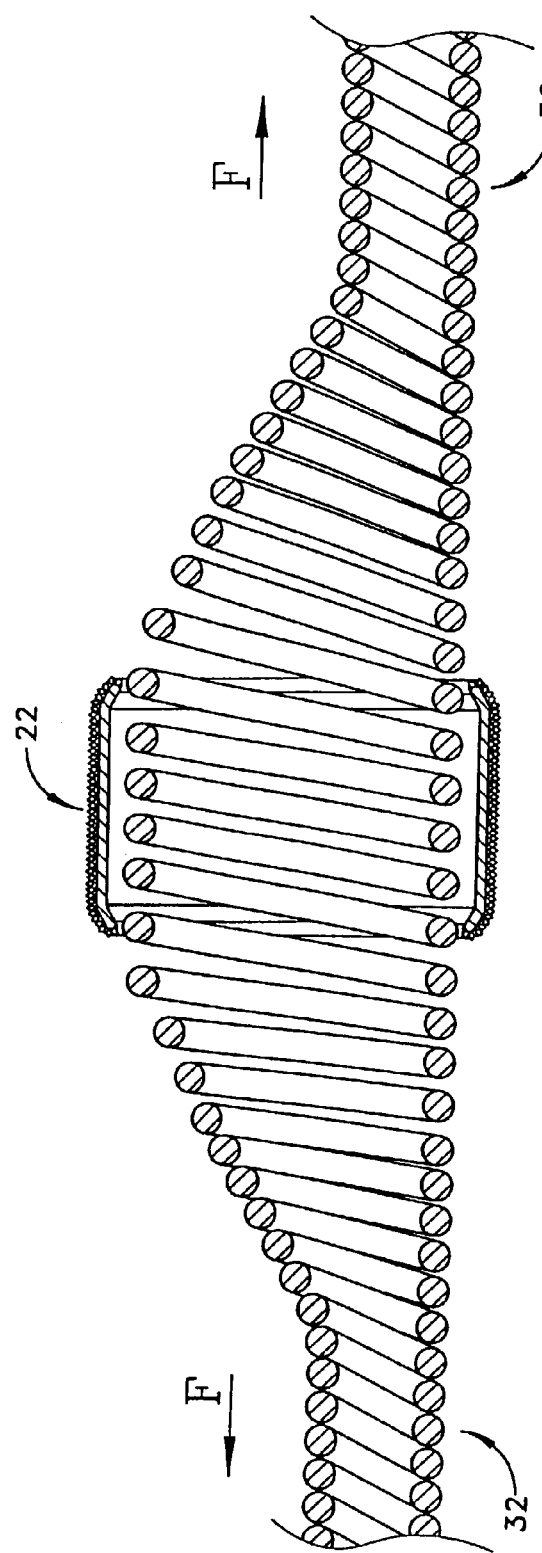
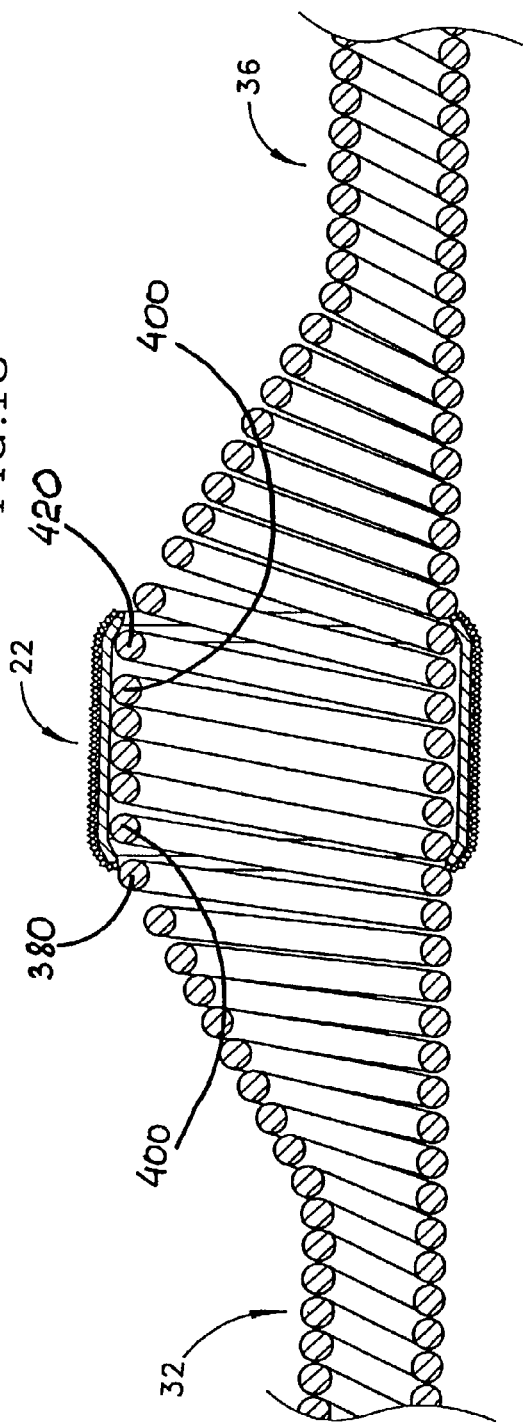

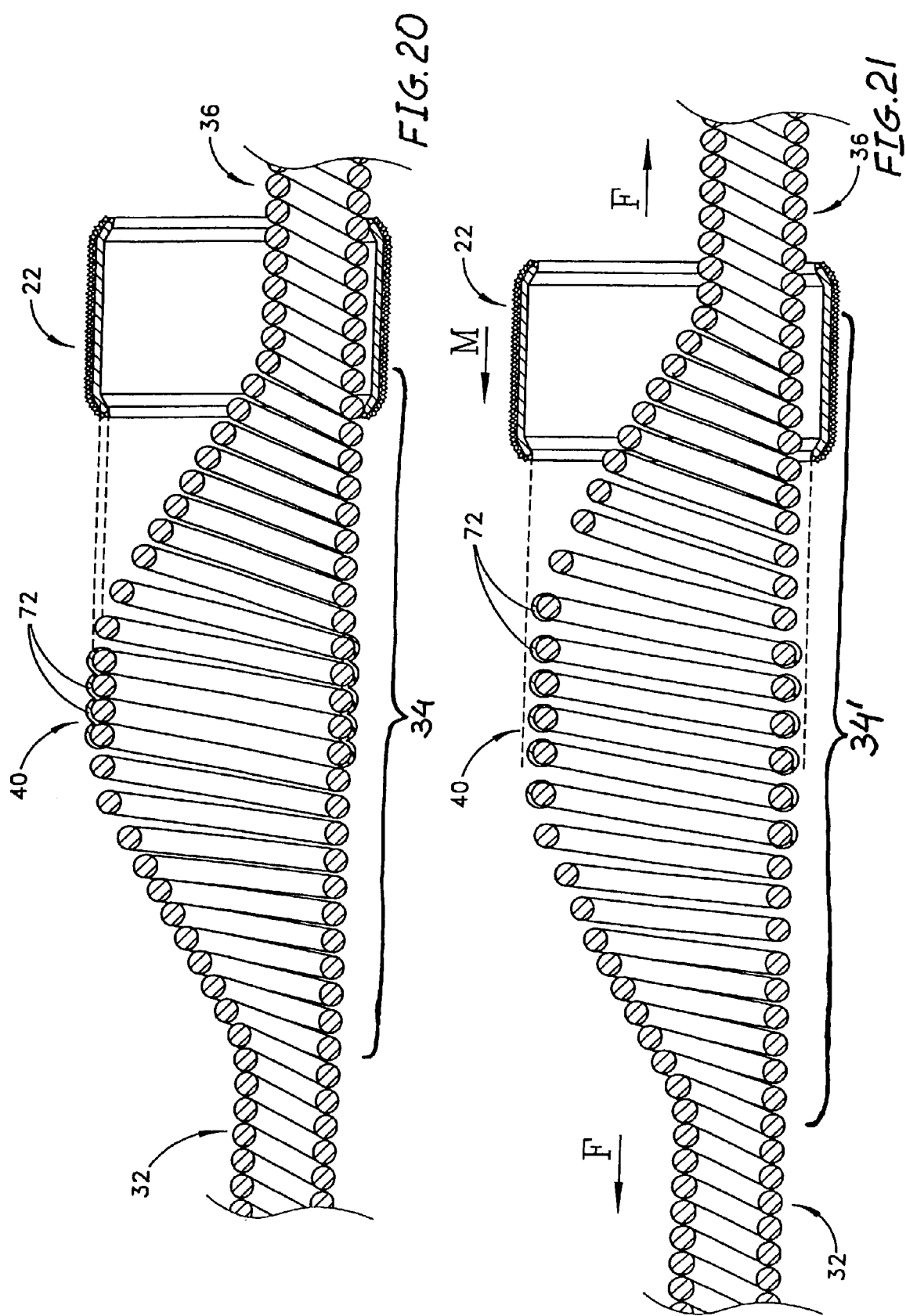

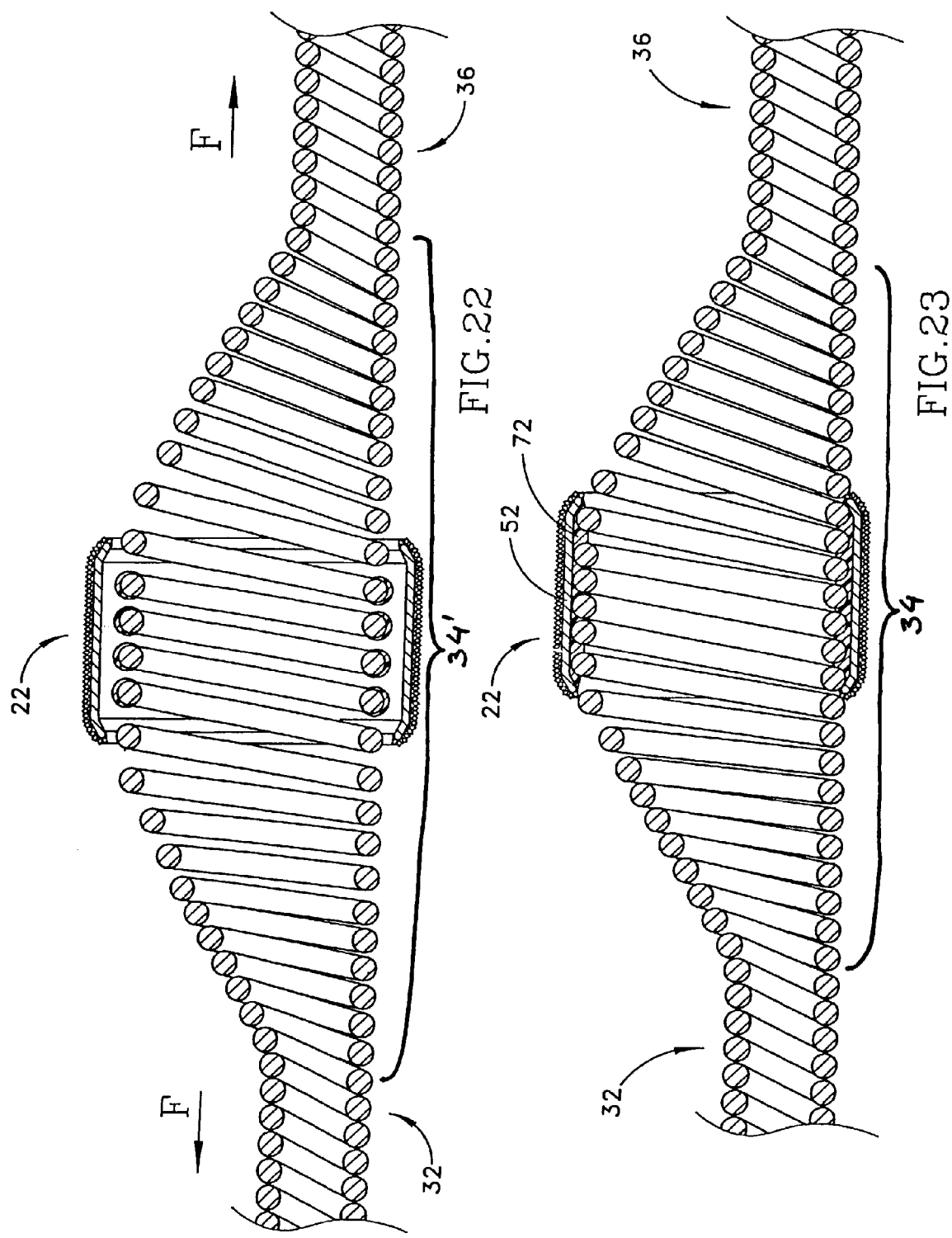

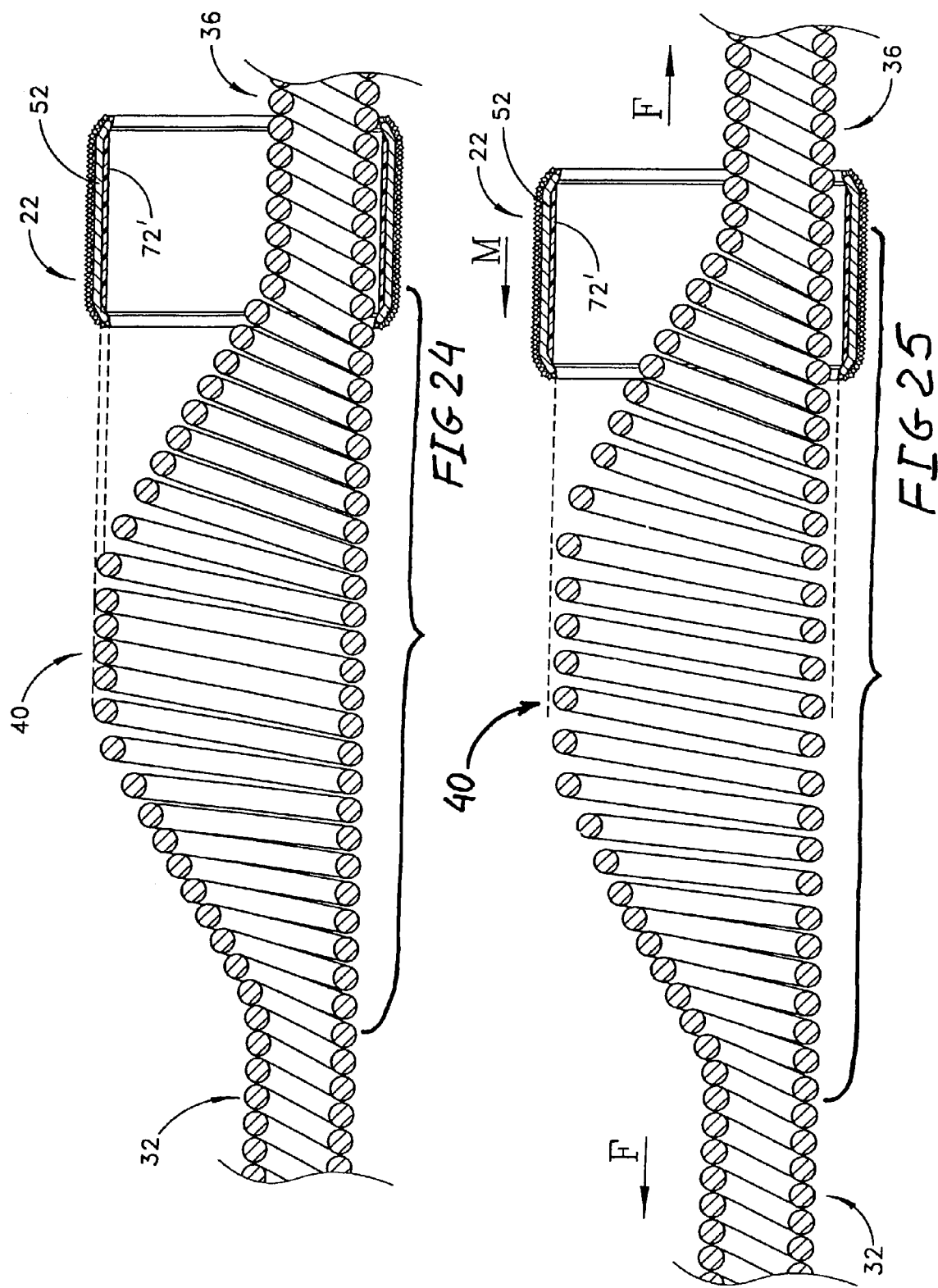

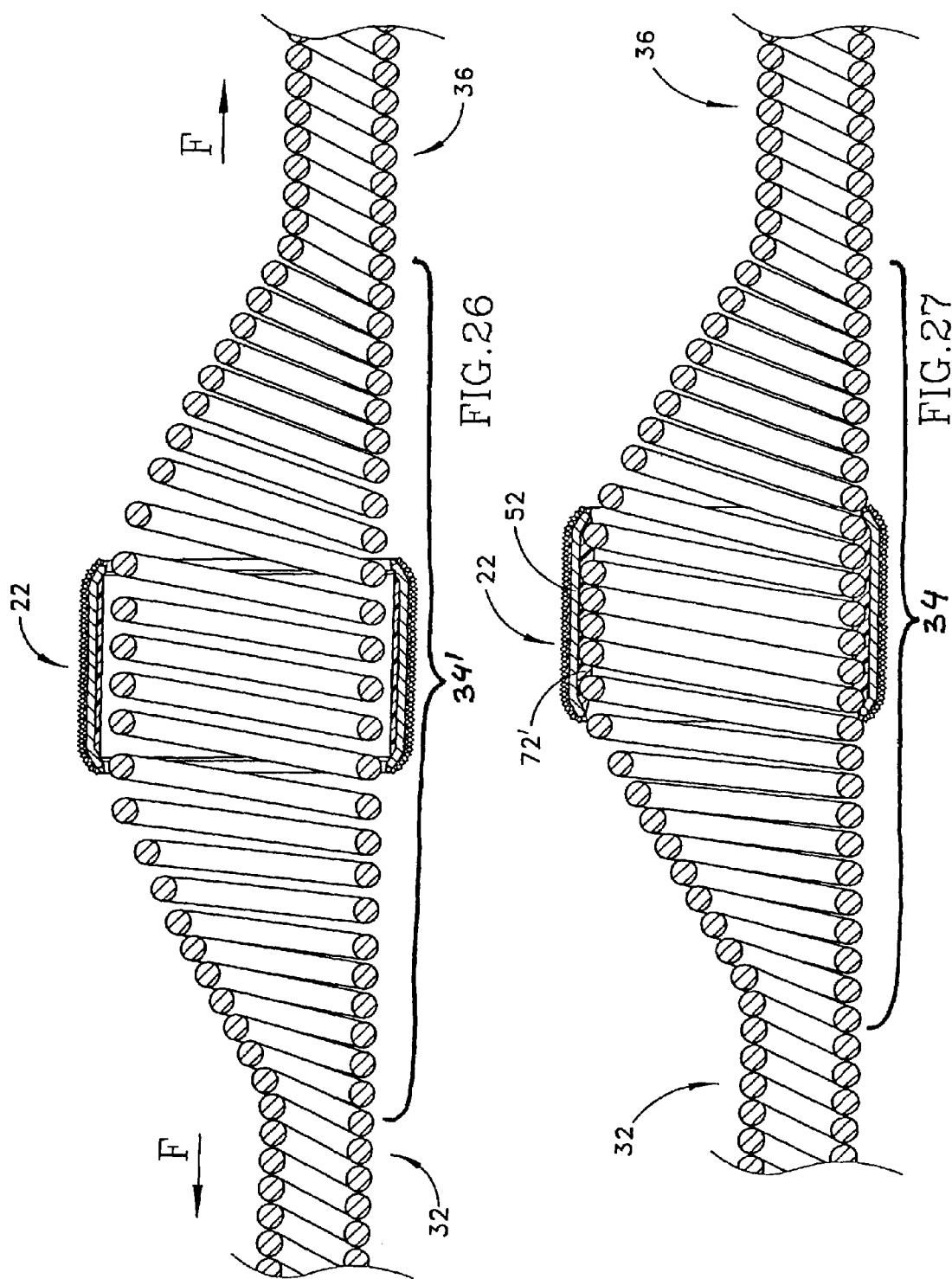

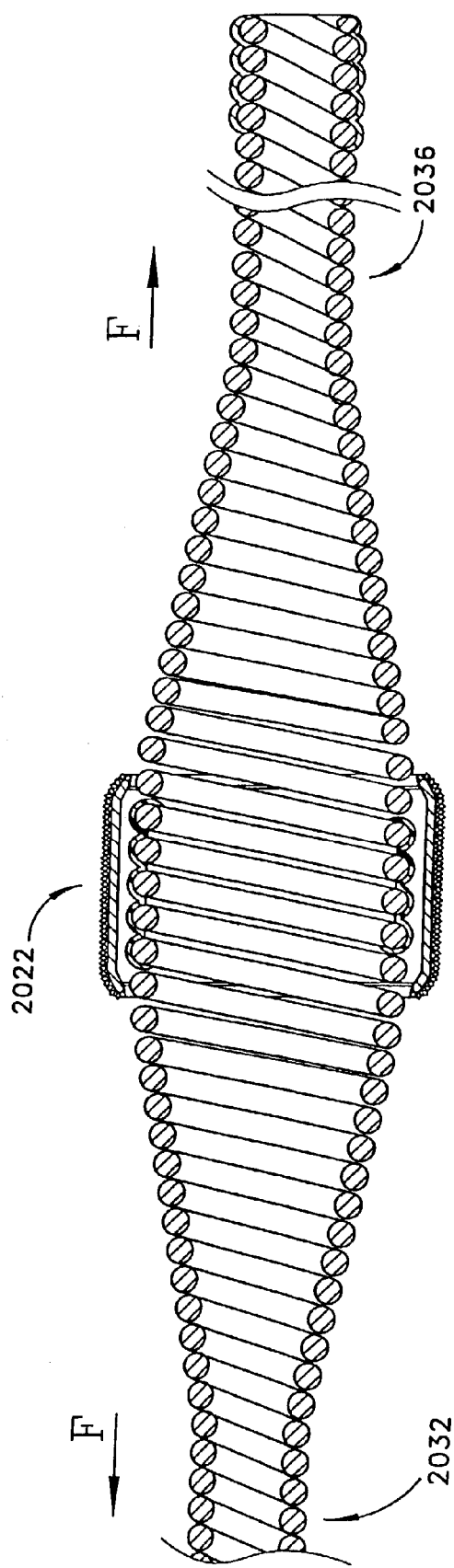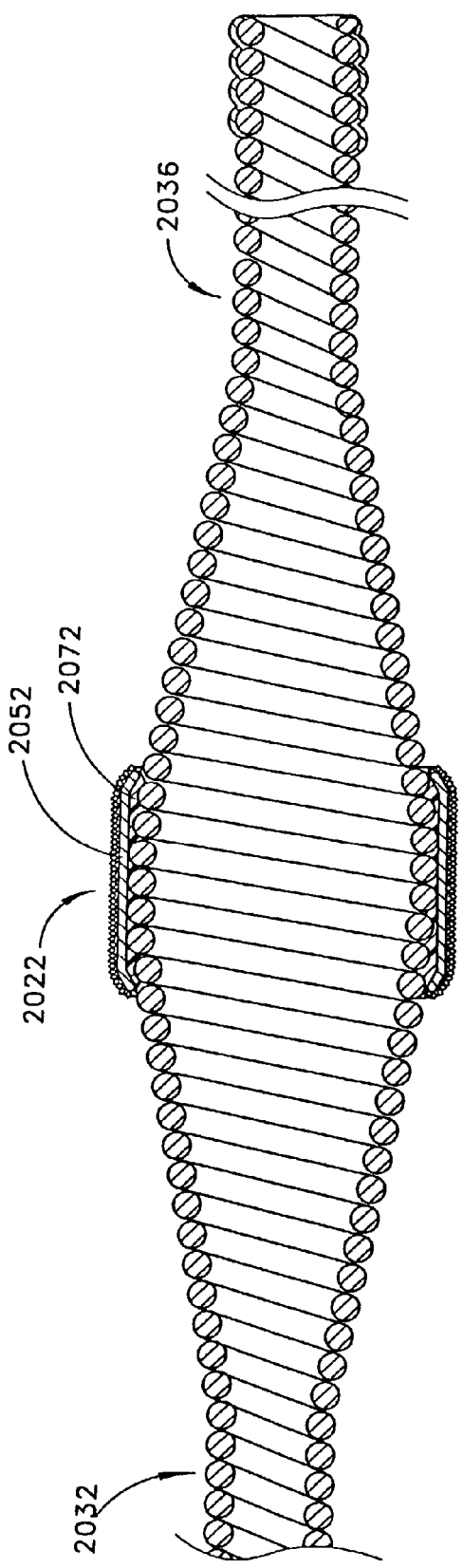

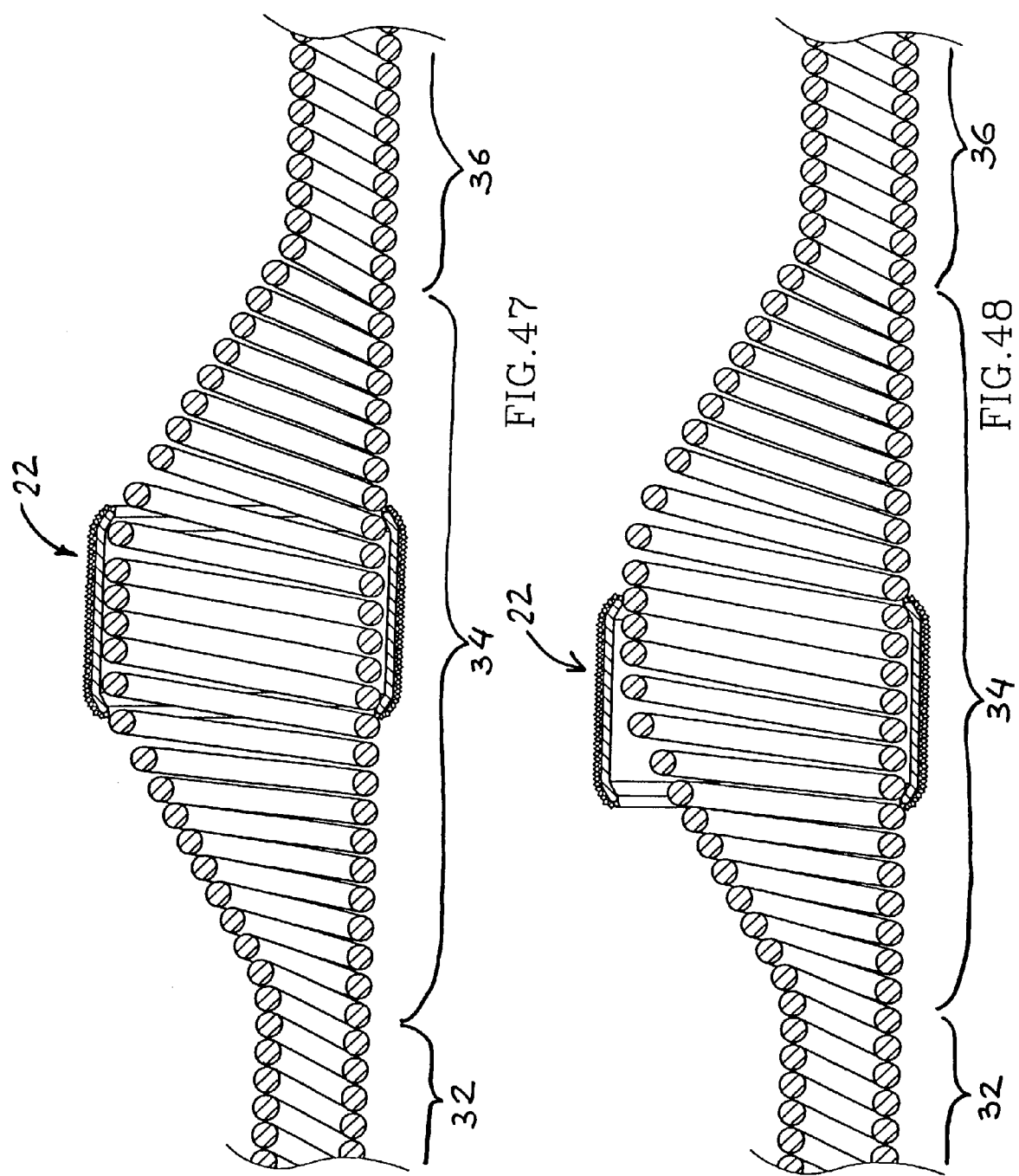

ROTATIONAL ANGIOPLASTY DEVICE WITH ABRASIVE CROWN

BACKGROUND OF THE INVENTION

1. Field of the Invention

The present invention relates to rotational angioplasty devices and, more particularly, to a rotational angioplasty device comprising a flexible drive shaft with an abrasive sleeve or crown mounted on the drive shaft.

2. Brief Description of Prior Developments

There are a number of different techniques and devices which have been developed for use in removal and/or repair of arteries and other similar body passages. One objective of some of the aforementioned devices and techniques is removal of atherosclerotic plaques from patient's arteries. Atherosclerosis is characterized by buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses. If left untreated, such stenoses can cause angina, hypertension, myocardial infarction, strokes and the like.

Rotational angioplasty procedures are a common technique for removing such stenotic material. Such procedures are used most frequently to commence the opening of calcified lesions in coronary arteries. Often the rotational angioplasty procedure is not used alone, but is followed by a balloon angioplasty procedure. This, in turn, may frequently be followed by placement of a stent to assist in keeping the artery open. For noncalcified lesions, balloon angioplasty most often is used alone to open the artery, with stents often placed to keep the artery open. Studies have shown, however, that a significant percentage of patients who have undergone balloon angioplasty and had a stent placed in an artery experience in-stent restenosis (i.e., blockage of the stent) which most frequently develops over a period of time as a result of excessive growth of scar tissue within the stent. Rotational angioplasty devices were utilized in removing the excessive scar tissue from the stents and, thereby were useful in providing assistance in restoring the patency of the arteries.

It should be understood that rotational angioplasty devices and rotational angioplasty procedures are often referred to as rotational atherectomy devices and rotational atherectomy procedures. These terms may be used interchangeably herein.

One example of a rotational angioplasty device is shown in U.S. Pat. No. 4,990,134 (issued to Auth), wherein a front or distal portion of a burr is covered with an abrasive cutting material such as diamond particles. The diamond coated burr is mounted at the distal end of a flexible drive shaft. The burr is rotated at high speeds (typically, e.g., in the range of about 140,000-180,000 rpm) while it is advanced across the stenosis. The burr has a solid cross-section and thus, as the burr is removing stenotic tissue, it also blocks blood flow through the artery. Once the burr has been advanced across the stenosis, the artery will have been opened to a diameter equal to or only slightly larger than the maximum outer diameter of the burr. A series of different size burrs may be utilized to open the artery to a desired diameter. U.S. Pat. No. 5,987,566 (issued to Shturman) shows another rotational angioplasty device having a drive shaft made from helically wound wires. A section of the drive shaft has an enlarged diameter. In one embodiment at least a front or distal segment of this enlarged diameter section is covered with an abrasive material to define an abrasive segment of the drive shaft. The enlarged diameter section is hollow. This Shturman Device of the '566 patent is capable of opening an artery only to a diameter about equal to the maximum diameter of the enlarged diameter section of the drive shaft, thereby providing results similar to the Auth Device of the '139 patent. The Shturman Device of the '566 patent possesses certain advantages over the Auth Device of the '139 patent because it is more flexible.

Another example of a rotational angioplasty device is provided in U.S. Pat. No. 6,132,444 (issued to Shturman et al.) which describes a rotational atherectomy device having a flexible, elongated, rotatable drive shaft with an asymmetric or eccentric enlarged diameter section. At least part of the eccentric enlarged diameter section has an abrasive surface which defines a tissue removing segment of the drive shaft. When placed within an artery against stenotic tissue and rotated at sufficiently high speeds (e.g. in the range of about 40,000 rpm to about 200,000 rpm) the eccentric nature of the enlarged diameter section of the drive shaft causes its abrasive segment to rotate in such a fashion as to open the stenotic lesion to a diameter substantially larger than the maximum diameter of the enlarged diameter section. Preferably the eccentric enlarged diameter section of the drive shaft has a center of mass spaced radially from the rotational axis of the drive shaft, facilitating the ability of the device to open the stenotic lesion to a diameter substantially larger than the maximum diameter of the enlarged diameter section. Typically this is achieved by constructing the enlarged diameter section of the drive shaft asymmetrically (i.e., spacing the geometric center of the eccentric enlarged diameter section of the drive shaft away from the rotational axis of the drive shaft). A drive shaft having an eccentric enlarged diameter tissue removal section with a diameter of not more than 2 mm is capable of opening stenotic lesions to a diameter equal to the original diameter of the coronary arteries (i.e., to a diameter of more than 3 mm) so that in a significant percentage of cases balloon angioplasty may not be needed to complete the procedure. The device is particularly useful for cleaning out partially blocked stents. The external coating or cover of abrasive material in Shturman Device described in '444 patent is applied directly to the wire turns of the helically wound wires, which make up the drive shaft. Application of abrasive material directly to the wire turns of the drive shaft is difficult and expensive due to a need to mask portions of the drive shaft which should not be coated with abrasive material. Direct deposition of abrasive material on the outer surface of the wire turns of the drive shaft is further complicated by any spaces between adjacent wire turns which are larger than what is acceptable for conventional abrasive material (diamonds) deposition techniques (e.g. electroplating). It should be also mentioned that electroplating of diamonds directly to the surface of the wire turns of the drive shaft requires chemical treatment of the surface of the wire turns prior to electroplating of the diamonds. Removing chemicals prior to or after electroplating of the diamonds is also difficult. The above described problems, which are associated with the direct deposition of abrasive material (diamonds) on the wire turns of the drive shaft made manufacture of the abrasive drive shafts unreliable and expensive. The present invention overcomes the problems associated with the direct deposition of the abrasive material on the wire turns of the drive shaft.

SUMMARY OF THE INVENTION

A rotational angioplasty device comprising a flexible, elongated drive shaft rotatable about an axis of rotation of the drive shaft, the drive shaft comprising one or more helically wound wires and having an eccentric enlarged diameter section and an abrasive crown mounted on the enlarged diameter section of the drive shaft.

BRIEF DESCRIPTION OF THE DRAWINGS

The foregoing aspects and other features of the present invention are explained in the following description, taken in connection with the accompanying drawings, wherein:

FIG. 9B is a table which lists representative dimensions of abrasive sleeves and drive shafts.

FIG. 16 is a partial cross-sectional view of the portion of the drive shaft and the abrasive sleeve taken along line 16-16 in FIG. 15;

FIG. 17 is another partial cross-sectional view of the portion of the drive shaft and the abrasive sleeve in FIG. 16 showing the portion of the drive shaft in a stretched condition during tissue removal section assembly in accordance with one method of the present invention;

FIG. 18 is still another partial cross-sectional view of the portion of the drive shaft and the abrasive sleeve in FIG. 16 showing the sleeve moved over the stretched portion of the drive shaft to its installed location during tissue removal section assembly;

FIG. 19 is a partial cross-sectional view of the portion of the drive shaft and the abrasive sleeve in FIG. 18 showing the drive shaft and the abrasive sleeve assembled in accordance with one method of the present invention;

FIG. 20 is a partial cross-sectional view of the portion of the drive shaft and the abrasive sleeve similar to the view of FIG. 16 but showing a bonding material deposited on wire turns of the drive shaft in accordance with a modified method of the tissue removal section assembly;

FIG. 21 is another partial cross-sectional view of the portion of the drive shaft and the abrasive sleeve in FIG. 20 showing the portion of the drive shaft in a stretched condition during tissue removal section assembly;

FIG. 22 is still another partial cross-sectional view of the portion of the drive shaft and the abrasive sleeve in FIG. 20 showing the sleeve moved over the stretched portion of the drive shaft to its installed location during tissue removal section assembly;

FIG. 23 is a partial cross-sectional view of the portion of the drive shaft and the abrasive sleeve showing the sleeve bonded (glued) to the drive shaft;

FIG. 24 is a partial cross-sectional view of the portion of the drive shaft and the abrasive sleeve similar to the view of FIG. 16, but showing a bonding material deposited on an inner surface of the abrasive sleeve in accordance with another modified method of the tissue removal section assembly;

FIG. 25 is another partial cross-sectional view of the portion of the drive shaft and the abrasive sleeve in FIG. 24 showing the portion of the drive shaft in a stretched condition during tissue removal section assembly;

FIG. 26 is still another partial cross-sectional view of the portion of the drive shaft and the abrasive sleeve in FIG. 24 showing the sleeve moved over the stretched portion of the drive shaft to its installed location during tissue removal section assembly;

FIG. 27 is a partial cross-sectional view of the portion of the drive shaft and the abrasive sleeve showing the sleeve bonded (glued) to the drive shaft.

FIGS. 36-39 are showing the same modified method of assembly of a tissue removal section of the drive shaft as shown in FIGS. 20-23, except for the tissue removal section in FIGS. 36-39 being symmetric;

FIGS. 47-48 are partial cross-sectional views of a drive shaft similar to the drive shaft in FIG. 1, respectively showing the abrasive sleeve in two locations on the shaft.

DETAILED DESCRIPTION OF THE PREFERRED EMBODIMENT

Figure 1A:
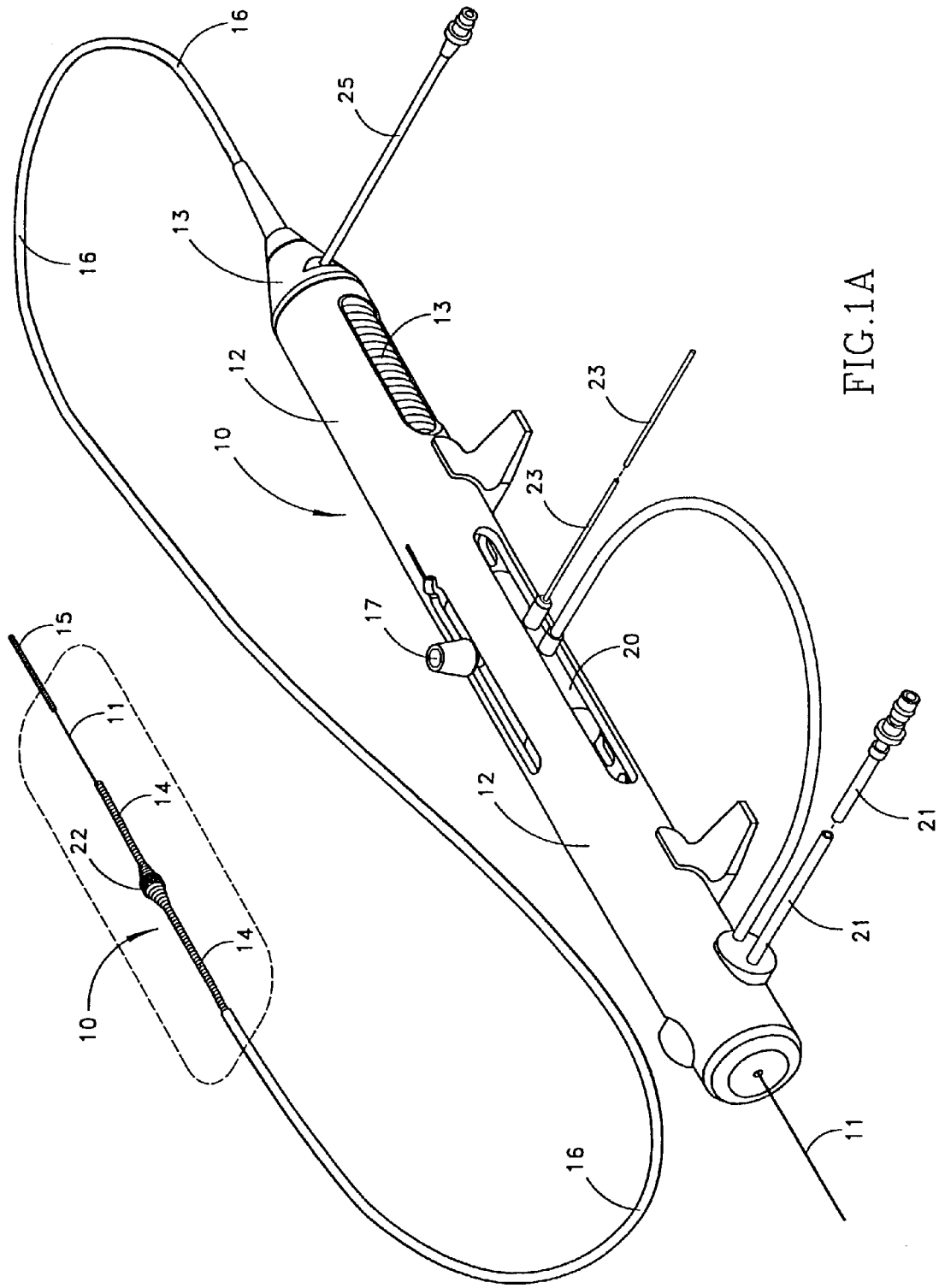
FIG. 1A is a perspective view of a rotational angioplasty device incorporating features of the present invention and showing the device advanced over a guide wire.

Referring to FIG. 1A, there is shown a perspective view of a rotational angioplasty device 10, incorporating features of the present invention. The angioplasty device 10 is shown advanced over a guide wire 11. Although the present invention will be described with reference to several embodiments as shown in the drawings, it should be understood that the present invention can be embodied in many more alternate forms of embodiments. In addition, any suitable size, shape or type of elements or materials could be used.

Figure 1B:
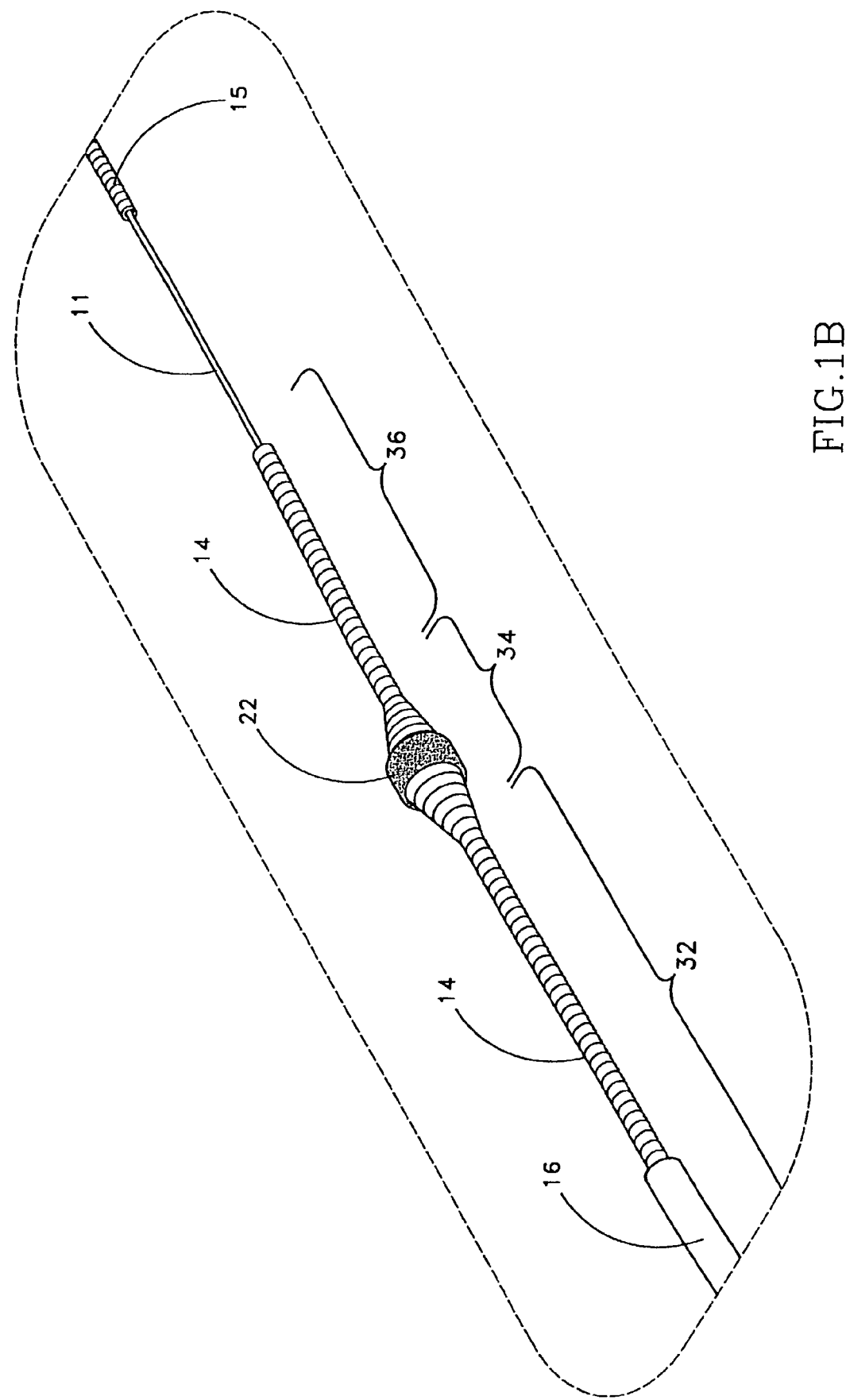
FIG. 1B is a magnified perspective view of a portion of the device shown in FIG. 1A.

The rotational angioplasty device of the invention generally comprises a handle portion 12, an exchangeable drive shaft cartridge 13, a flexible elongated drive shaft 14, and an elongated tube 16. The handle portion 12 may have a prime mover carriage 20 which carries a prime mover (not shown) for rotating the drive shaft 14. A compressed gas driven turbine is usually used as the prime mover. The flexible elongated drive shaft 14 is operatively connected at one end to the to the prime mover carried by the prime mover carriage 20. The flexible elongated drive shaft 14 carries an abrasive tissue removal sleeve or crown 22 mounted on the drive shaft about 30 mm away from the other end of the drive shaft. Most of the drive shaft 14 is held within the elongated tube 16, with an enlarged diameter section 34 of the drive shaft extending out of the elongated tube 16 and carrying the abrasive sleeve or crown 22. FIG. 1B provides a magnified view of that portion of the drive shaft, which extends from the elongated tube 16. The rotational angioplasty device 10 has a lumen extending through the drive shaft 14, the exchangeable drive shaft cartridge 13 and the handle portion 12 of the device thereby allowing angioplasty device 10 to be advanced over the guide wire 11. During operation of the rotational angioplasty device 10, the prime mover rotates the drive shaft over the guide wire 11. Both the prime mover and the drive shaft may be moved axially back and forth over the guide wire 11 as will be described in greater detail below.

Still referring to FIGS. 1A and 1B, the guide wire 11 is generally comprised of an elongated flexible wire. Such wire is usually provided with a floppy distal end portion 15. A suitable guide wire for use with the rotational angioplasty device of the present invention is commercially available from Boston Scientific Corporation, Natick, Mass. However, the rotational angioplasty device of the present invention may be used with any other suitable guide wire, or with no guide wire if desired.

The exchangeable drive shaft cartridge 13 and the handle portion 12 shown in FIG. 1A are described in U.S. Pat. Nos. 6,024,749 and 6,077,282, issued to Shturman. However, in alternate embodiments the handle portion and/or the exchangeable drive shaft cartridge of the rotational angioplasty device may be of any other suitable type, including the type(s) commercially available from Boston Scientific Corporation, Natick, Mass.

The handle portion 12 may be made of plastic or metal, and may have any desired shape. The prime mover carriage 20 carries a gas turbine or any other suitable rotational prime mover capable of rotating the drive shaft at speeds of up to about 200,000 rpm or more. The gas turbine may be operated with compressed gas, and may be capable of rotating the drive shaft 14 from 0 rpm to its maximum rotational speed of about 200,000 rpm or more. The prime mover carriage 20 is slidably mounted in the handle portion 12 allowing the prime mover to be moved back and forth relative to the handle portion 12. In the preferred embodiment a suitable flexible compressed gas line 21 supplies compressed gas to a guide wire break (not shown) and to the gas turbine carried by the prime mover carriage 20. A fiber optic tachometer is usually used to monitor the rotational speed of the gas turbine. One such fiber optic tachometer is described in U.S. Pat. No. 6,039,747 issued to Shturman. A single optical fiber 23 shown in FIG. 1A and described in Shturman '747 patent may extend from the prime mover carriage 20 and may be connected to a controller (not shown). The rotational angioplasty device may also include a control knob 17, which is connected to the prime mover carriage 20 and allows an operator to move the prime mover back and forth relative to the handle portion 12. The elongated tube 16 is made of any suitable medical grade elastomeric material. The elongated tube 16 at its proximal end is secured within a distal portion of the exchangeable drive shaft cartridge 13 (the terms distal and proximal are related hereinafter to the handle portion 12, the exchangeable drive shaft cartridge 13, the flexible drive shaft 14 and other components of the rotational angioplasty device). The lumen in the elongated tube 16 is sized and shaped so that the drive shaft 14 extending through the elongated tube 16 may be rotated and/or moved back and forth relative to the elongated tube substantially without resistance. As seen in FIG. 1A, a fluid supply line 25 may be also connected to the distal portion of the exchangeable drive shaft cartridge 13 for introducing a cooling or lubricating solution (e.g. saline) into the elongated tube 16.

Figure 2:
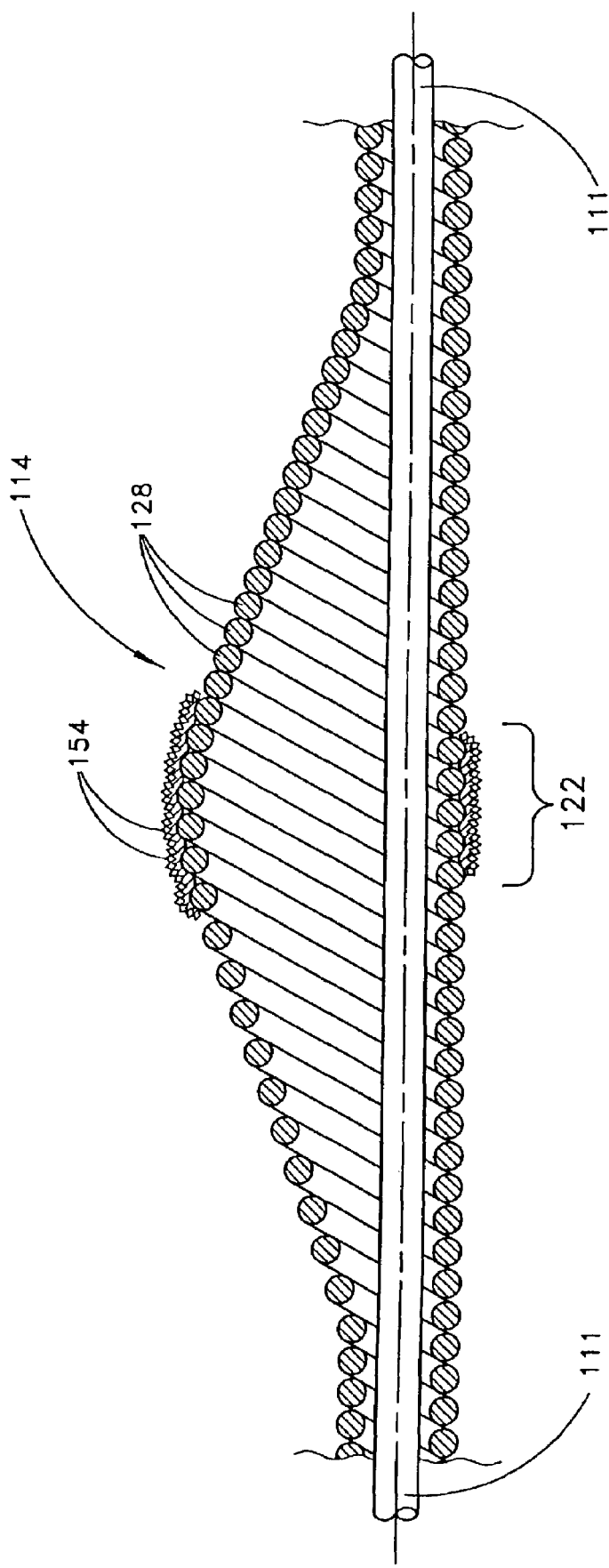
FIG. 2 is a partial cross-sectional view of the eccentric tissue removal section of the rotational angioplasty device of the prior art.
Figure 4:
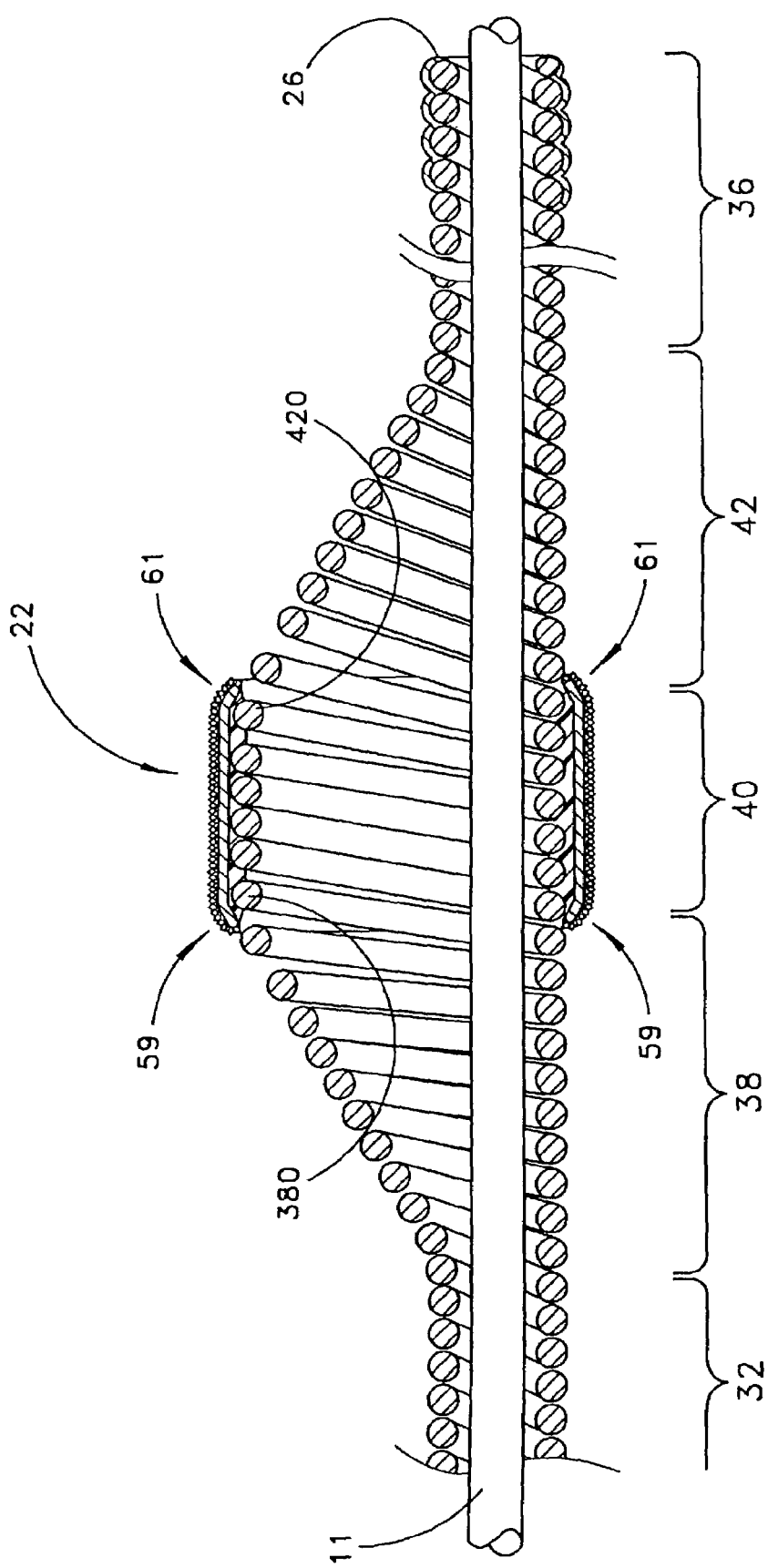
FIG. 4 is a partial cross-sectional view of the portion of the drive shaft and tissue removal section taken along line 4-4 in FIG. 3, the abrasive sleeve or crown of the present invention shown bonded to the drive shaft.

As can be seen by comparing FIGS. 2 and 4 the eccentric abrasive drive shaft 114 of the prior art (see FIG. 2) and the eccentric abrasive drive shaft of the present invention (see FIG. 4) are substantially similar except for the abrasive sleeve or crown 22 mounted on the enlarged diameter section 34 of the drive shaft of the present invention.

As shown in FIG. 2 an abrasive segment 122 of the eccentric abrasive drive shaft 114 of the prior art is formed by direct deposition of abrasive material (e.g. diamonds 154) on the wire turns 128 of the drive shaft. The drive shaft 114 is rotated around a guide wire 111. The eccentric abrasive drive shaft of the prior art is described in U.S. Pat. No. 6,132,444 issued to Shturman and is incorporated by reference herein in its entirety.

All of the embodiments of the present invention will be described below with reference to a tri-filar drive shaft, although the present invention applies equally to any suitable drive shaft formed from any number of helically wound wires or to any other suitable flexible drive shaft.

Figure 3:
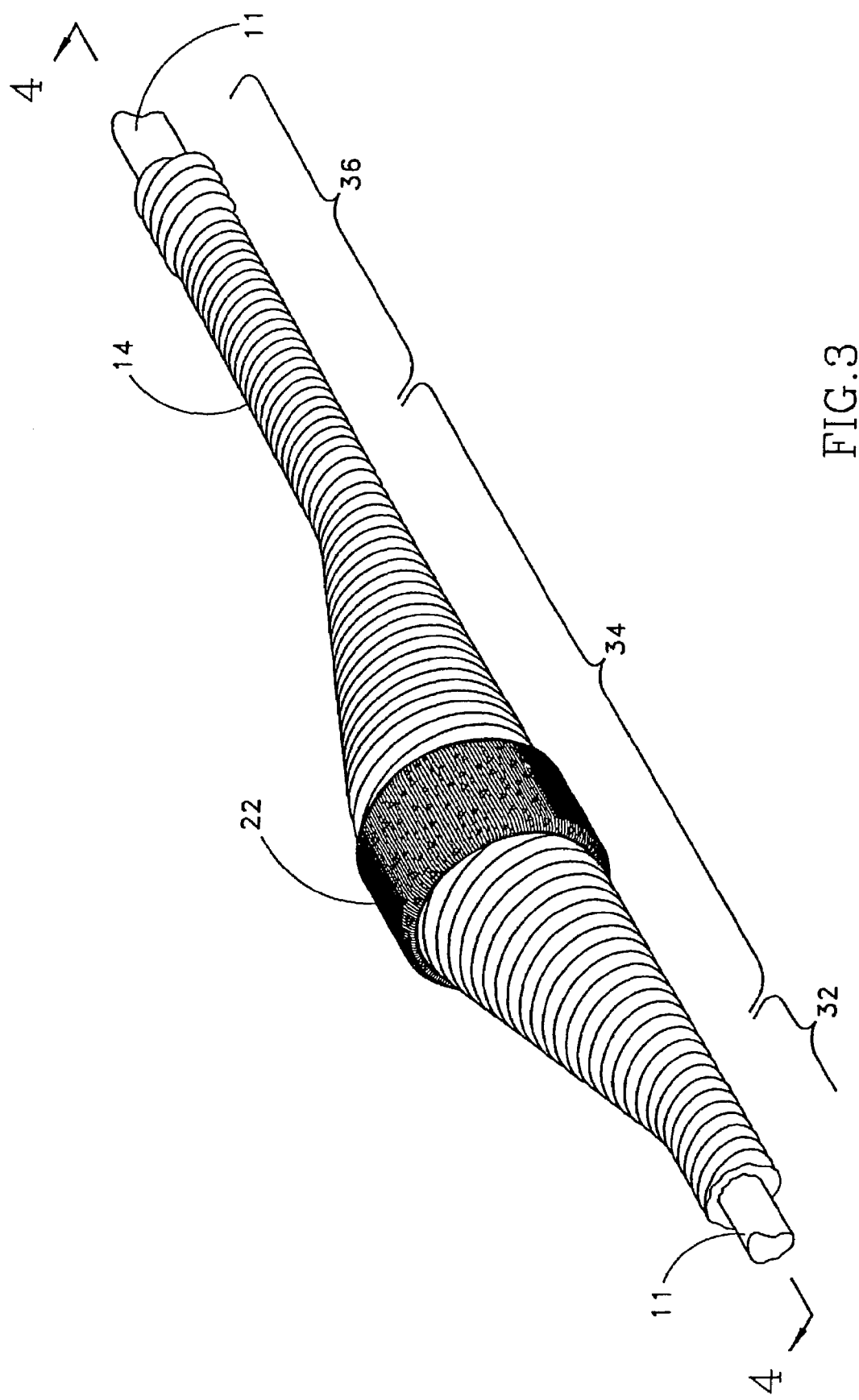
FIG. 3 is a partial perspective view of a portion of the drive shaft of the rotational angioplasty device where an abrasive sleeve or crown of the present invention is a part of an eccentric tissue removal section.

As shown in FIGS. 1A and 1B and in FIGS. 3 and 4 an abrasive segment of the eccentric drive shaft 14 of the present invention is formed by mounting the abrasive sleeve or crown 22 on the eccentric enlarged diameter section 34 of the drive shaft.

As shown in FIG. 1B and FIGS. 3 and 4, the flexible drive shaft 14 has an elongated proximal section 32, an enlarged diameter section 34, and an elongated distal section 36. The enlarged diameter section 34 comprises a proximal (conical or substantially conical) portion 38, an intermediate portion 40, and a distal (conical or substantially conical) portion 42. The intermediate portion 40 of the enlarged diameter section of the drive shaft may be very short and, if needed, may be simply formed by a junction between the conical proximal portion 38 and conical distal portion 42 of the enlarged diameter section of the drive shaft. In the assembled rotational angioplasty device, as shown in FIG. 1A, the elongated proximal section 32 of the drive shaft 14 extends from the prime mover (gas turbine) to the enlarged diameter section 34. This elongated proximal section 32 for the most of its length is located within the elongated tube 16 and may be completely withdrawn within the tube 16. The elongated distal section 36 of the drive shaft 14 extends distally from the enlarged diameter section 34 to the distal end 26 of the drive shaft.

The drive shaft 14 may have any suitable length. The wires making up the drive shaft are preferably made out of stainless steel wire of any suitable tensile strength such as for example 400 kpsi or more (e.g. "Hyten" wire produced by Fort Wayne Metals Research Products Corp., Fort Wayne, Ind.). The wires are substantially the same, each having a diameter about 0.006 inch, though wires having a diameter of for example about 0.005, or 0.004 inch as well as wires of any suitable smaller or larger diameter may be used. The drive shaft is formed generally by winding the wire or wires around a suitable wire mandrel. As described in U.S. Pat. No. 6,132,444 issued to Shturman the enlarged diameter section 34 of the drive shaft is formed by winding the drive shaft around an enlarged diameter element of the mandrel. The enlarged diameter element of the mandrel has a biconical shape and is fixed around the wire mandrel. The enlarged diameter element of the mandrel is usually made from material different from which the wire mandrel and drive shaft 14 are made from. As described in more detail in the U.S. Pat. No. 6,132,444 the enlarged diameter element of the drive shaft may be made from brass and dissolved in a solution of Nitric Acid after the drive shaft 14 has been wound and heat treated. The maximum diameter of the enlarged diameter element of the mandrel is selected so as to generate a desired maximum outer diameter of the enlarged diameter section 34 of the drive shaft. As will be described in greater detail below, in the preferred embodiment, the enlarged diameter section 34 of the drive shaft 14 may have the abrasive sleeve or crown 22 with a maximum outer diameter 22D (see FIG. 7) of, e.g. about 1.07 mm, or about 1.25 mm, or about 1.7 mm, or about 1.93 mm as desired. It is desirable to make the maximum outer diameter 22D of the abrasive sleeve or crown 22 of the drive shaft 14 such that it would pass through the lumen of the smallest guiding catheter (not shown), which may be selected by a physician for the advancement of the drive shaft 14 to the stenotic lesion in a patent's vessel. Therefore, the maximum diameter 22D of the abrasive sleeve or crown 22 of the drive shaft 14 has to be somewhat smaller than the inner diameter of the guiding catheter. Physicians may use guiding catheters having a size for example of 6 F (French), 7 F, 8 F or 9 F, though any other suitable size guiding catheter may be used. The drive shaft 14 which may be used with a 6 F guiding catheter may have a maximum outer diameter 22D (see FIG. 7) of up to 1.5 or even 1.6 mm, while drive shafts with a maximum outer diameter 22D larger than 1.6 mm, usually would require 7 F, 8 F, or even larger size guiding catheters. It should be noted that guiding catheters produced by different manufacturers may have the same outer diameters but may differ in their inner diameters, so that a drive shaft having a maximum diameter of about 1.6 mm may be advanced through the 6 F guiding catheter produced by one manufacturer and may not be advanced through a 6 F guiding catheter produced by another manufacturer.

It should be understood that the term "the maximum diameter of the abrasive sleeve or crown 22" may be used interchangeably with a the term "the maximum diameter of the tissue removal element 22."

Still referring to FIGS. 3 and 4, the outer diameters of successive consecutive wire turns making up the proximal conical portion 38 of the enlarged diameter section 34 increase distally in a substantially linear manner (i.e. increase at a constant rate). Conversely, the distal conical portion 42 of the enlarged diameter section 34 has consecutive wire turns with an outer diameters which decrease distally in a substantially linear manner (i.e. decrease at a substantially constant rate) between successive consecutive wire turns. As seen in FIG. 4 the intermediate portion 40 of the enlarged diameter section 34 has consecutive wire turns with substantially the same outer diameters. As seen in FIGS. 3 and 4, in the preferred embodiment of the present invention the elongated distal section 36 of the drive shaft 14 extends distally from enlarged diameter section 34. The elongated distal section 36 extends to the distal end 26 of the drive shaft 14. The elongated distal section 36 in this embodiment has substantially the same diameter as the elongated proximal section 32 immediately adjacent the enlarged diameter section 34 of the drive shaft. Accordingly, the wire turns at the proximal and distal ends of the proximal and distal conical sections 38 and 42 have substantially the same outer diameters. The elongated distal section 36 of the drive shaft is shown in FIGS. 3 and 4 as having a representative length, and in the preferred embodiment the length of distal section 36 may be anywhere from about 22 mm to about 26 mm. In alternate embodiments, the length of the distal section may be greater than 26 mm or less than 22 mm as desired. The drive shaft 14 has a hollow lumen, which may accommodate the guide wire 11. The drive shaft 14 also has an axis of rotation which is generally coincident with axis of the guide wire 11 (see FIGS. 3 and 4) about which the drive shaft is rotated (e.g. by a gas turbine). In accordance, with one embodiment of the present invention, the enlarged diameter section 34 of the drive shaft 14 is asymmetric or eccentric relative to a longitudinal or rotational axis of the proximal 32 and the distal 36 sections of the drive shaft and hence asymmetric or eccentric with respect to the general rotational axis of the drive shaft. The enlarged diameter section may be made eccentric as described in U.S. Pat. No. 6,132,444 or by any other suitable method.

Figure 5:
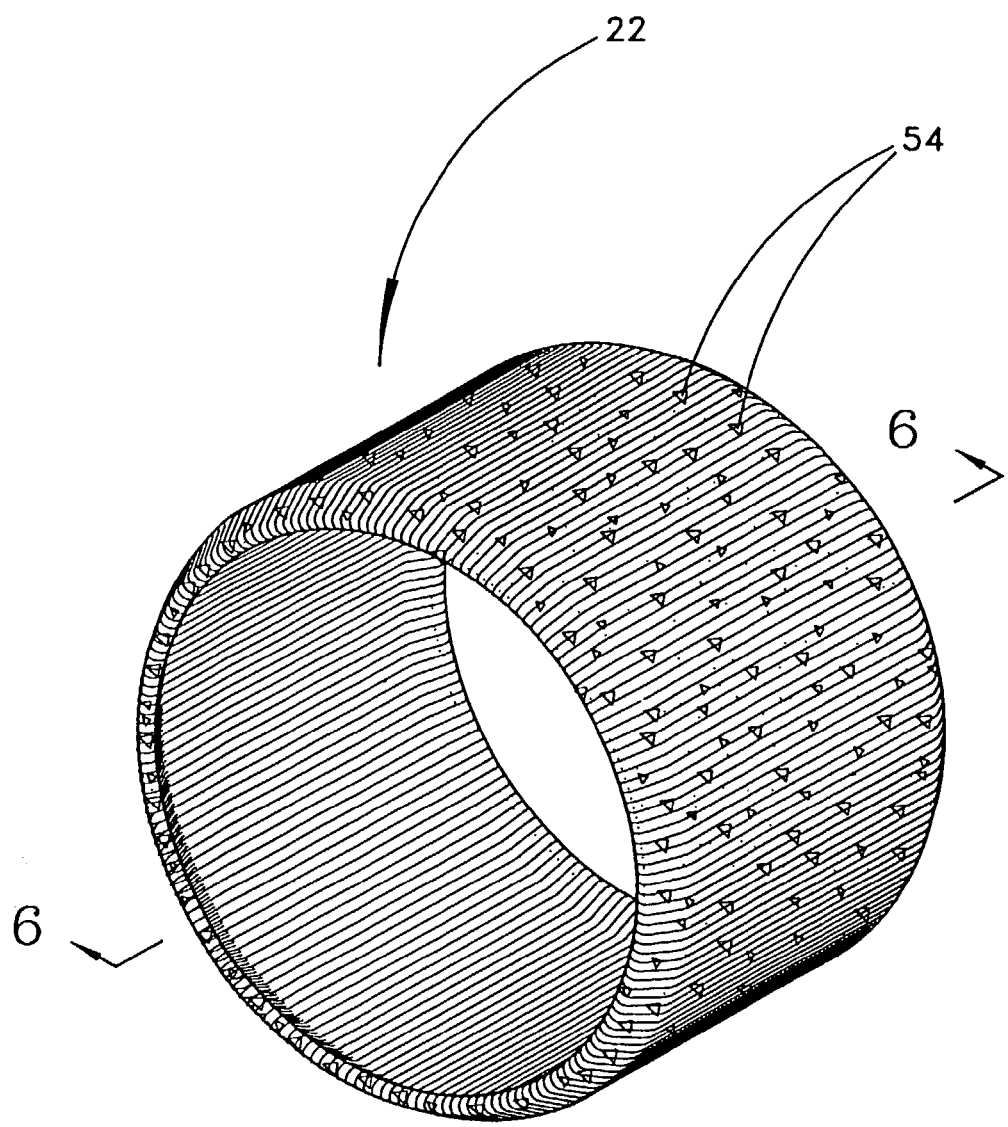
FIG. 5 is a perspective view of an abrasive sleeve or crown of the tissue removal section of the drive shaft shown in FIG. 4.
Figure 6:
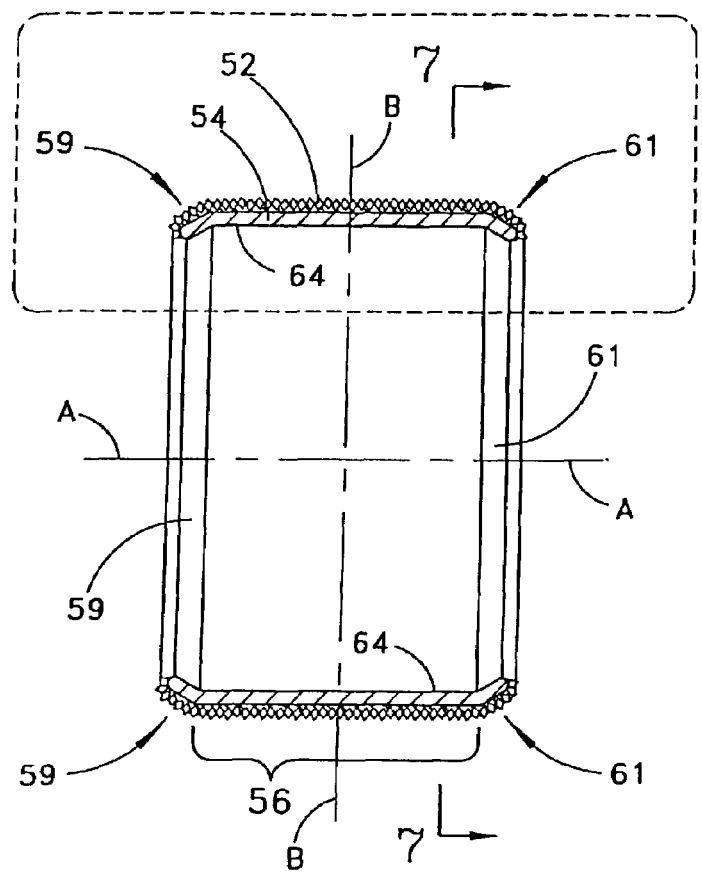
FIG. 6 is a longitudinal cross-sectional view of the abrasive sleeve or crown taken along line 6-6 in FIG. 5.
Figure 8:
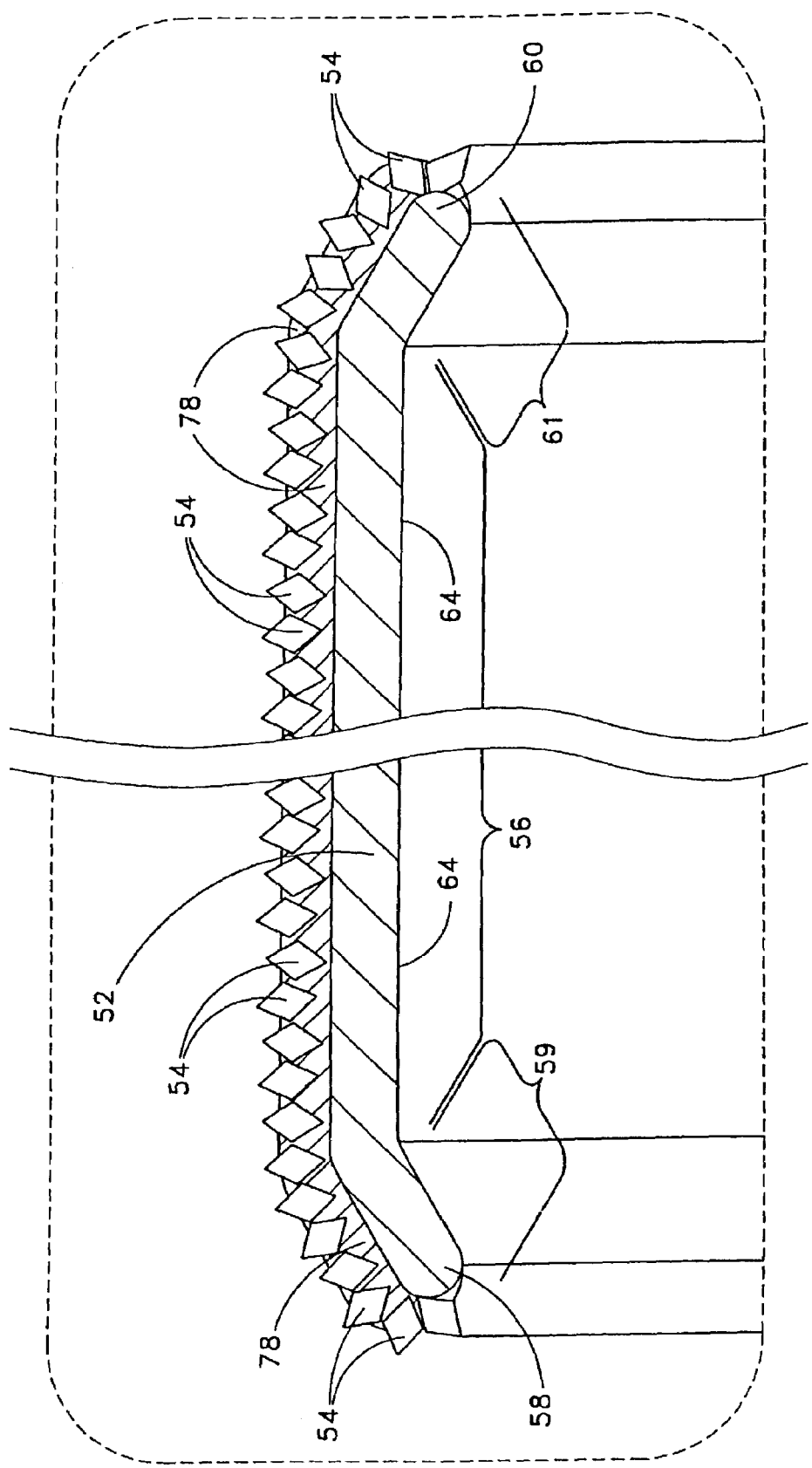
FIG. 8 is a partial magnified cross-sectional view of a portion of the abrasive sleeve or crown as indicated in FIG. 6.

FIGS. 3 and 4 show an abrasive sleeve or crown 22 mounted on the eccentric enlarged diameter section 34 to form the tissue removal section of the rotational angioplasty device 10. Referring now to FIG. 5, there is shown a perspective view of the abrasive sleeve 22. FIG. 6 shows a longitudinal cross-sectional view of the abrasive sleeve 22 taken along line 6-6 in FIG. 5. The abrasive sleeve 22 comprises a core sleeve 52 and abrasive 54. The core sleeve 52 is preferably a one piece member having a generally cylindrical shape. In this embodiment the sleeve is made of metal such as for example stainless steel, carbon steel, brass, copper alloy, a high radio opacity alloy, or any other suitable metal. Examples of suitable high radio opacity alloys are platinum alloys, paladium alloys, tantalum alloy, nickel alloy, or tungsten alloy. In alternate embodiments the sleeve may be made from any suitable non-metallic material such as composite material, elastomeric material, or a plastic. As seen in FIGS. 6 and 8, the core sleeve 52 has a substantially flat main section 56 which terminates in swaged or inwardly tapered opposing ends 58 and 60. The swaged ends 58 and 60 are defined by circumferential lips 59 and 61 turned inwards relative to a longitudinal or rotational axis A-A of the sleeve (i.e. turned downwards relative to the outer circumference of the sleeve). FIG. 6 shows the lip 59 and the lip 61 turned inwards and extending continuously around the sleeve circumference, although in alternate embodiments the lips may comprise a number of separate sections equally distributed around the circumference of the sleeve. FIG. 8 shows a magnified view of a portion of the abrasive sleeve 22. As better seen in FIG. 8, in the preferred embodiment of this invention both lips 59 and 61 form sections which are inwardly inclined relative to the substantially cylindrical main section 56 of the sleeve 52.

Figure 7:
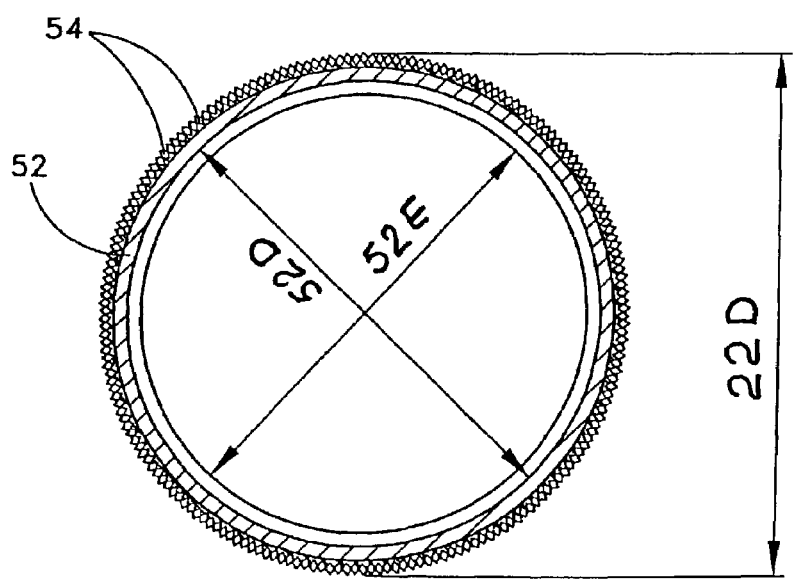
FIG. 7 is a transverse cross-sectional view of the abrasive sleeve or crown taken along line 7-7 in FIG. 6.

As can be realized from FIGS. 7 and 8 in the preferred embodiment of the invention the inwardly turned lips or sections 59 and 61 at the opposing ends of the abrasive sleeve are symmetrical with respect to a center line B-B, which is perpendicular to the longitudinal axis A-A of the sleeve 22. The inward inclined sections at the opposing ends of the sleeve 22 extend circumferentially around the main section 56 of the sleeve. In alternate embodiments, the lips at the ends of the sleeve may have a curved shape. The "turned in" lips 59 and 61 extend from the main section 56 of the core sleeve 52 to define an annular recess in the core sleeve 52. The inner surface of the main section 56 of the core sleeve 52 forms the bottom of the annular recess in the sleeve 22. Thus, in the preferred embodiment of the invention the bottom of the annular recess in the sleeve 22 is substantially flat as shown in FIGS. 6 and 8. The inner surface 64 of the main section 56 of the core sleeve 52 has a diameter 52D sized to form a close or tight fit around the wire turns of the intermediate portion 40 of the enlarged diameter section of the drive shaft (see FIG. 4). As seen in FIG. 7, the diameter 52E of the openings at each of the opposing swaged ends 58 and 60 of the core sleeve 52 is smaller than the diameter of the inner surface 64 of the main section 56 of the sleeve. In the preferred embodiment, the swaged ends 58 and 60 are generally symmetrical with respect to the center line B-B and hence the diameters of the openings at the opposing ends of the sleeve are substantially the same. In alternate embodiments, the sleeve may have asymmetrical ends with different diameter of the openings at the ends of the core sleeve 52. In still other alternate embodiments, the core sleeve 52 may not have ends which are swaged or stamped or otherwise "turned in".

In the preferred embodiment of the invention, the diameter 52E of the openings at the opposing ends of the core sleeve 52 is sized to form an interference fit with the wire turns of the conical portions 38 and 42 or with the wire turns of the intermediate portion 40 of the enlarged diameter section 34 of the drive shaft.

As seen in FIG. 4, the sleeve 52 preferably has a length sufficient to extend over all wire turns of the intermediate portion 40 of the enlarged diameter section 34 of the drive shaft 14. The circumferential lips 59 and 61 at the swaged ends 58 and 60 of the abrasive sleeve 22 may overhang one or more transitional wire turns 380, 420 at the corresponding interfaces of the proximal 38 and distal 42 conical portions with the intermediate 40 portion of the enlarged diameter section of the drive shaft. Alternatively, the circumferential lips at the swaged ends of the abrasive sleeve 22 may be sized longitudinally to be disposed around the proximal and distal wire turns of the intermediate portion 40 of the enlarged diameter section of the drive shaft. In yet another embodiment the circumferential lips at the swaged ends of the abrasive sleeve 22 may be sized longitudinally to be disposed around wire turns of the conical portions 38 and 42, these wire turns being located sufficiently close to the intermediate portion 40 of the drive shaft.

Referring again to FIGS. 6-8, the abrasive elements (diamonds) 54 of the abrasive sleeve 22 are disposed on the outside of the core sleeve 52. The abrasive particles (diamonds) 54 may be attached to the core sleeve 52 by any suitable means. By way of example, in the preferred embodiment, a layer of nickel 78 may be used for bonding diamond particles to the outer surface of the core sleeve 52. In the process of bonding diamond chips to the core sleeve 52 the diamond chips become embedded in the nickel with only relatively small portions of the diamond chips sticking out of the nickel 78 and forming abrasive surface of the abrasive sleeve or crown 22.

It should be noted that, in alternate embodiments, the abrasive and bonding materials may be made from any other suitable materials to allow formation of an abrasive on the sleeve. For example, in the case where the abrasive is diamond powder, the diamond powder may be brazed on to the sleeve. In another alternate embodiment the outer surface of the sleeve 22 itself may be provided with abrasive properties without depositing any kind of abrasive material on the outer surface of the core sleeve 52. As seen in FIGS. 6-8, the abrasive particles (diamonds) 54 are located on the outer surface of the core sleeve 52. The layer of abrasive particles 54 extends onto the outer surface of the lips 59 and 61 at the opposing swaged ends 58 and 60 of the core sleeve 52. FIG. 8 provides a magnified view of the layer of abrasive particles 54 on a representative portion of the abrasive sleeve 22. The distribution or configuration of the layer of abrasive particles on the lips 59 and 61 is symmetric with respect to the center line B-B of the core sleeve 52. As seen in FIGS. 6 and 8, the layer of abrasive particles 54 extends substantially uniformly on the outer surface of the lip 59 and on the outer surface of the lip 61. The layer of abrasive particles 54 also covers a portion of an edge of the lip 59 and a portion of an edge of the lip 61. In the preferred embodiment both lips 59 and 61 have generally rounded edges. In the preferred embodiment no abrasive material is disposed on the inner surface of the lip 59 and on the inner surface of the lip 61. There is also no abrasive material on the inner surface of the core sleeve 52. The mean thickness of the layer of the diamonds 54 (including electroplated nickel substrate) may be in the range of about 30-60 microns although the abrasive layer may have any other suitable thickness. In the preferred embodiment diamond powder (diamond grit) with 30-40 microns chip size has been utilized and it is desirable that majority of diamond chips stick out of nickel or another bonding or braising material for only about 5-10 microns. It should be noted that diamond grit having a size range of about 20-30 microns was also successfully utilizes by authors of this invention.

The maximum outer diameter of the enlarged diameter portion of the drive shaft, and the maximum outer diameter of the abrasive sleeve 22 are preferably selected so that for each commercially available guiding catheter size (e.g. 6 F, 7 F, 9 F) there is a maximum diameter drive shaft of this invention that may be advanced through such commercially available guiding catheter.

Figure 9A:
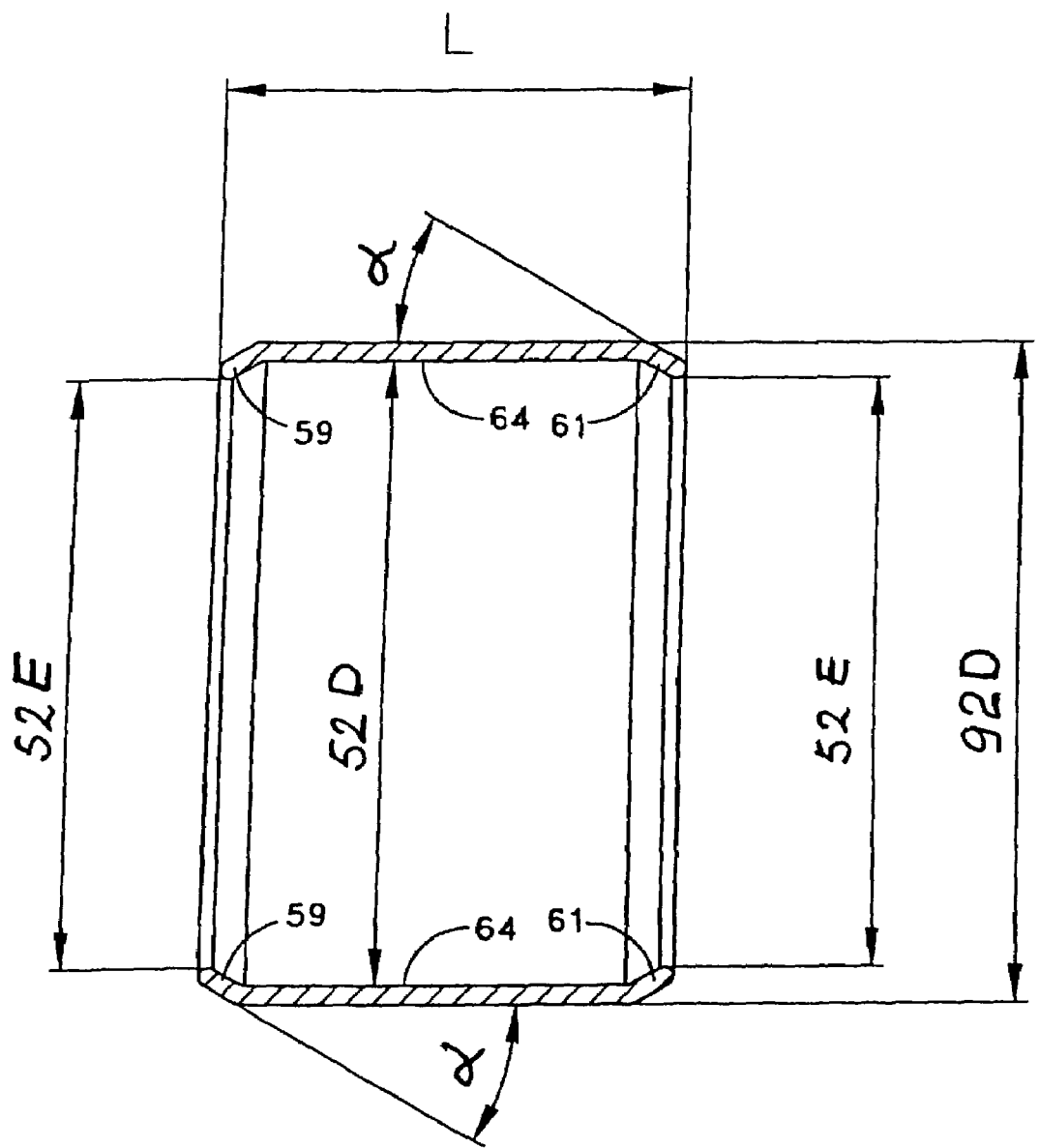
FIG. 9A is a longitudinal cross-sectional view of the core sleeve or crown taken along line 9A-9A in FIG. 14.

FIG. 9B in a table format lists representative dimensions of four sizes of drive shafts and abrasive sleeves of the invention. The reference numbers and letters (92D, 52D, 52E, L and α) associated with the deminsions for the core sleeve 52 are shown in FIG. 9A. It should be noted that the representative dimensions listed in FIG. 9B are provided for modified embodiment of the drive shaft 1014 shown in FIG. 28.

The dimensions listed in FIG. 14A are merely examples of suitable dimensions for the different diameter abrasive sleeves and drive shafts used in accordance with the present invention. In alternate embodiments, the sleeve and drive shaft may have any other suitable dimensions. For example, in the case when the inner lumen of a given size guiding catheter becomes larger than what is now available, then the sleeve(s) outer diameter(s) may be increased accordingly. The length of the sleeve may also be increased or decreased as desired, as well as any of the other dimensions listed in FIG. 9B. In the preferred embodiment, the core sleeves 52 of different outer diameters (different sizes) have substantially the same wall thickness of about 0.05 mm, though in alternate embodiments the different diameter (size) sleeves may have any other suitable wall thickness of thicknesses.

Figure 10:
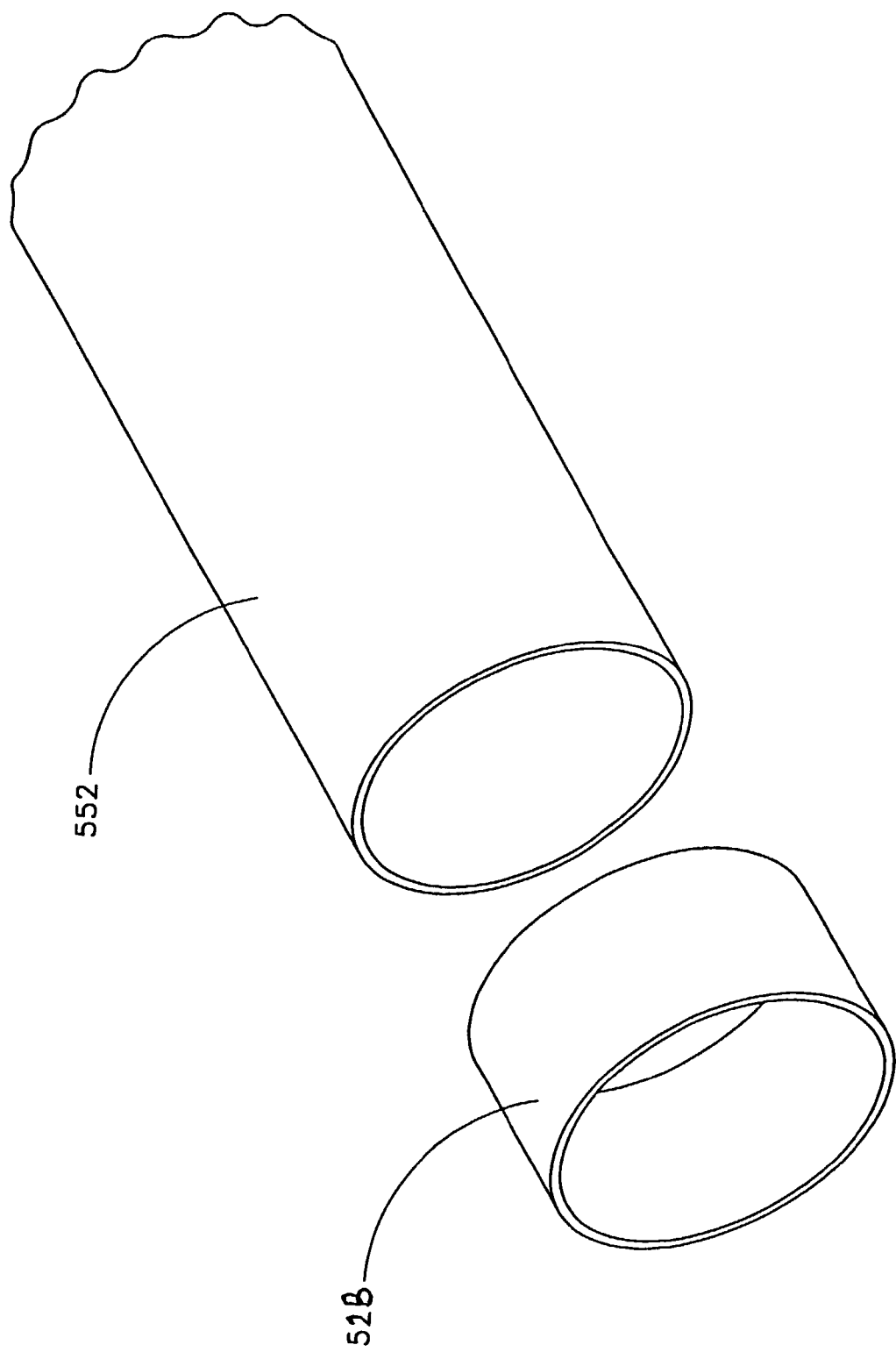
FIG. 10 is a perspective view showing a tubing stock and a sleeve blank cut off from the tubing stock.
Figure 11:
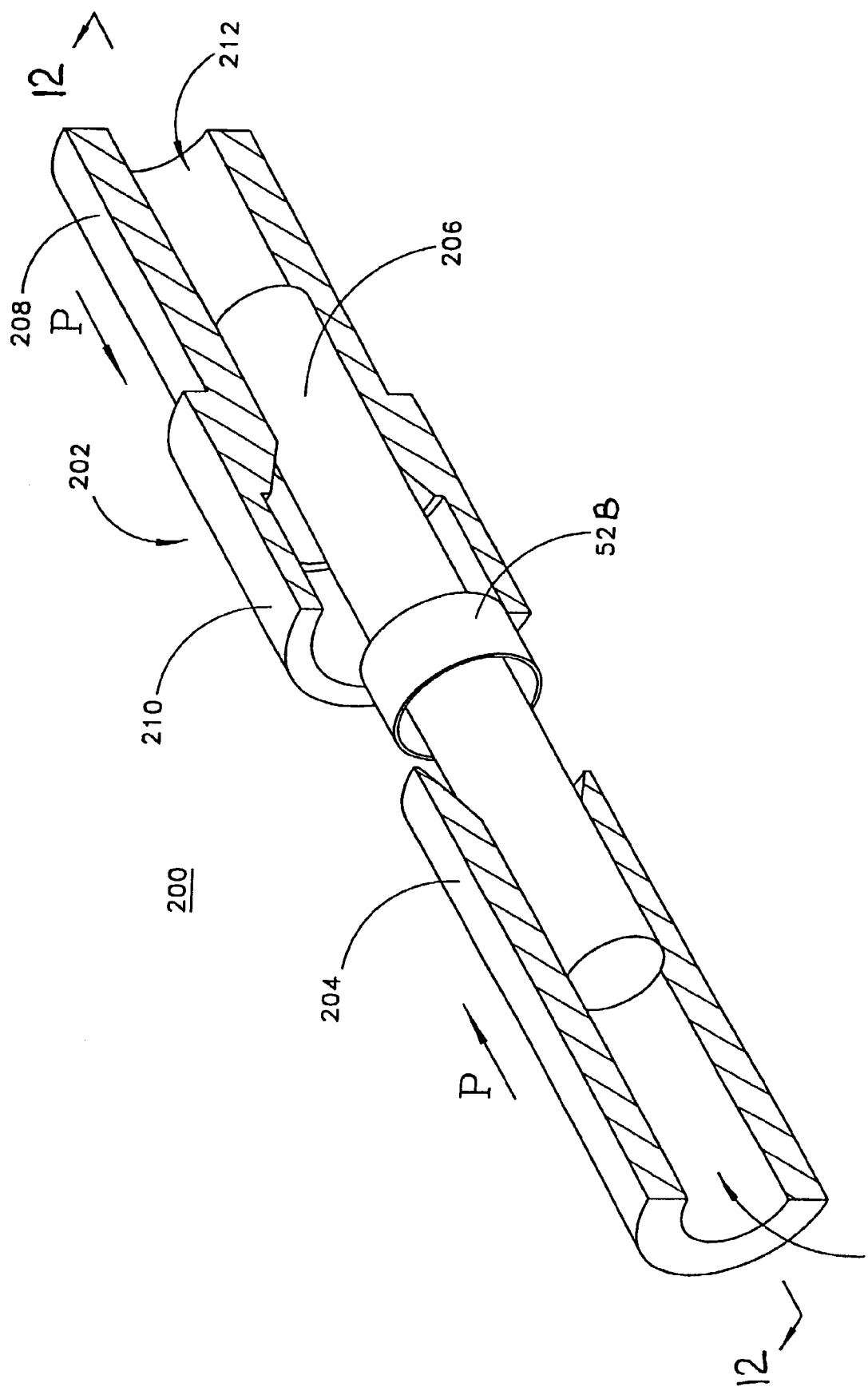
FIG. 11 is a cross-sectional perspective view of a die assembly for forming the sleeve with an unstamped sleeve placed within the die assembly, the die assembly being shown in an open position.
Figure 12:
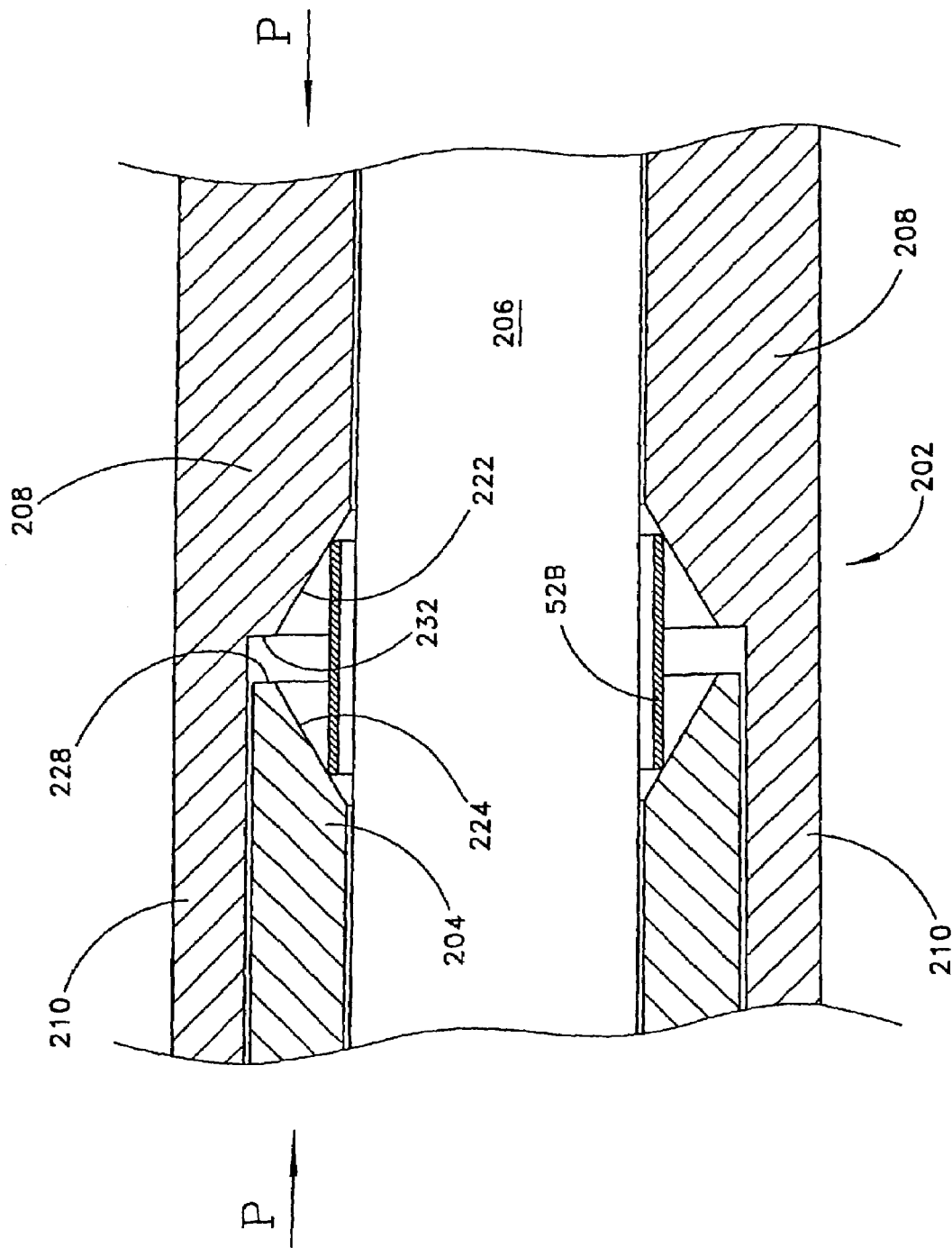
FIG. 12 is a cross-sectional view of the die assembly and the unstamped sleeve taken along line 12-12 in FIG. 11, the die assembly being shown in an intermediate position.
Figure 13:
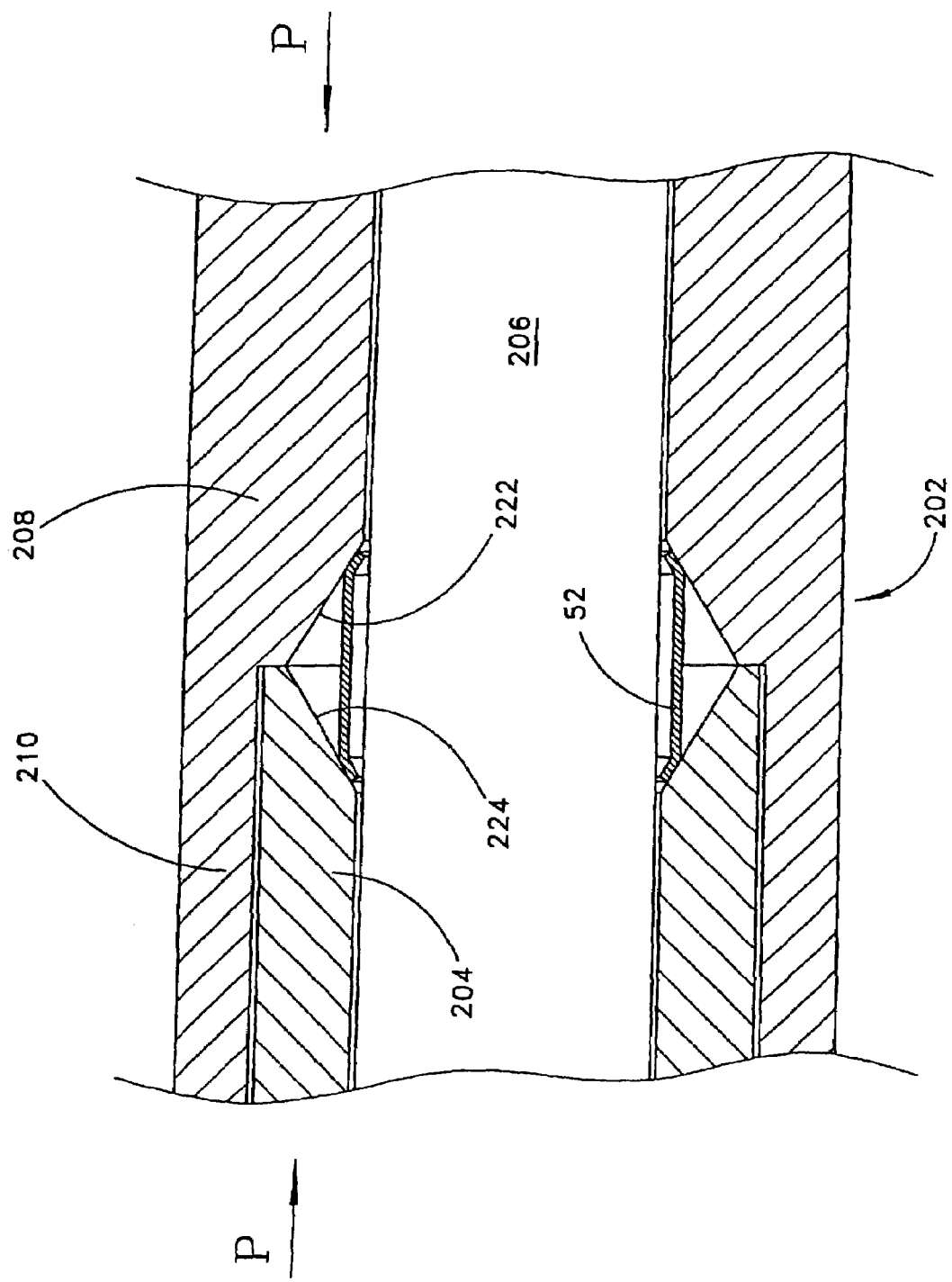
FIG. 13 is another cross-sectional view of the die assembly showing the die assembly closed and the sleeve stamped.

Referring now the FIGS. 10-14, fabrication of the core sleeve 52 may be performed generally as described below. The core sleeve 52 (see FIG. 9A) is preferably formed by cutting the stock tube 552 (see FIG. 10) in sections 52B suitably sized to form blanks from which the sleeve core 52 is fashioned. One such sleeve blank 52B is shown in FIG. 10. The sleeve blank 52B may then be placed in a suitable stamping die to form the sleeve 52. FIGS. 11-13 show an example of a suitable stamping die assembly 200 with the sleeve blank 52B. In FIG. 11 the stamping die assembly 200 is shown in an initial or open position. In FIGS. 12 and 13, the die assembly 200 is shown respectively in intermediate and closed positions. The stamping die assembly 200, generally comprises die 202, complementing die 204, and guide shaft 206. The die 202 has a base section 208 and a socket section 210 which extends from the base section.

In the preferred embodiment of the invention all components of the die assembly 200 are made from metal. The die 202 has a conical portion 222 and the complementing die 204 has a complementing conical portion 224 (see FIGS. 11 and 12). The conical portion 224 terminates in an annular step of flange 228 (see FIG. 12). This annular flange 228 forms a stop when the complementing die 204 is inserted into the socket section 210 of the die 202.

The angles of the conical portions 222 and 224 are set to correspond to the inclinations of the "turned in" lips 59 and 61 of the sleeve 52 (see FIGS. 6, 8 and 9A).

As can be realized from FIG. 11, the core sleeve blank 52B is placed over the guide shaft 206 before both ends of the guide shaft 206 are inserted into corresponding bores 212 and 220 of the dies 202 and 204.

FIG. 12 shows the die assembly 200 in its intermediate position where conical portions of the dies 202 and 204 are already touching the sleeve blank 52B, but not stamping it. The stamping die assembly 200 may be placed in this position into a suitable clamp press (not shown).

Figure 14:
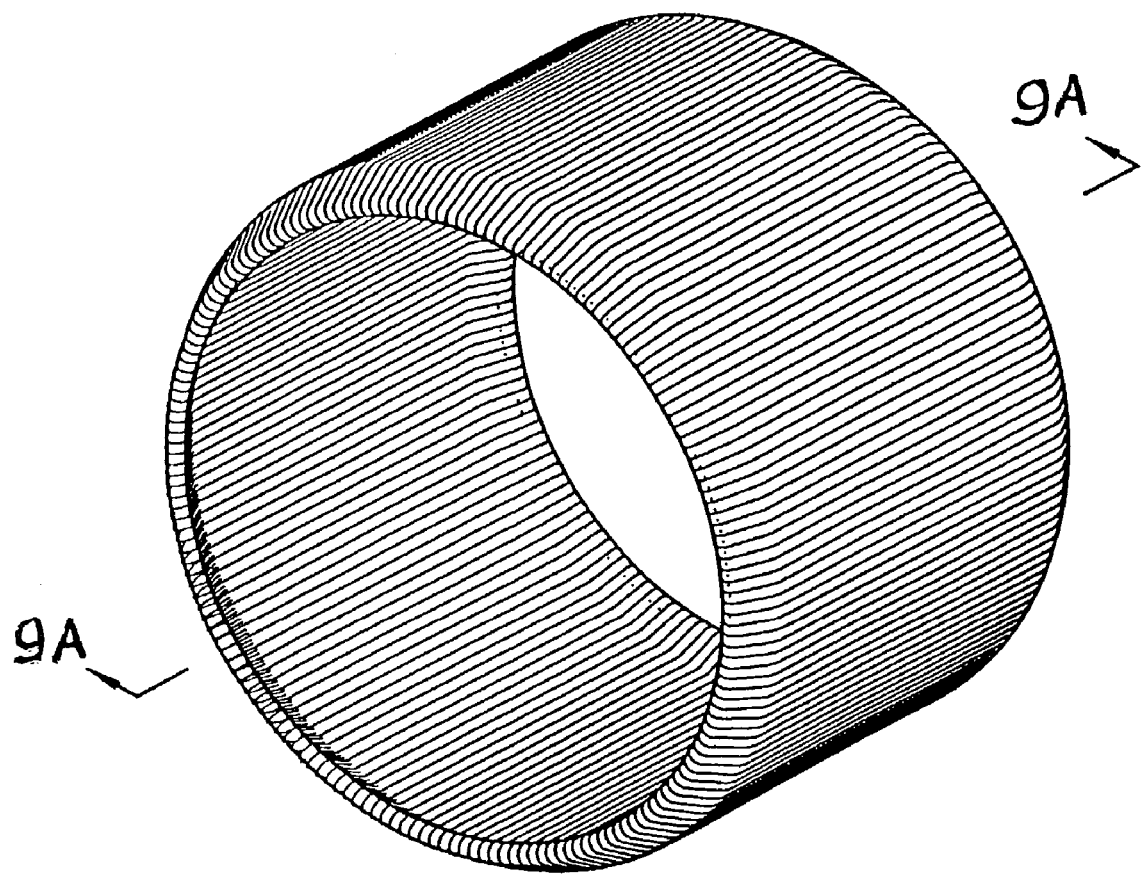
FIG. 14 is a perspective view of the stamped sleeve.

The clamping press or other clamping device applies opposing axial forces (in the direction indicated by arrows P in FIGS. 11-13 on the die 202 and complementing die 204. The axial forces cause the die 202 and complementing die 204 to close upon each other eventually reaching closed position shown in FIG. 13. Guide shaft 206 maintains alignment of the complementing die 204 with the die 202 as the two dies are closed from the initial open position, shown in FIG. 11, to the closed position shown in FIG. 13. As can be realized from FIG. 12, as the dies 202 and 204 are pressed together in the direction of arrows P, the conical portions 222 and 224 act as alignment means for sleeve blank 52B automatically positioning the sleeve blank 52B concentric with respect to the conical portions 222 and 224. The opposing forces, in the direction of arrows P, on the dies 202 and 204 continue to be applied until the dies reach the closed position shown in FIG. 13. In this position, the front rim 228 of the complementing die 204 is abutted against flange 232 of the die 202. This stops the complementing die 204 from being inserted further into the socket section of the die 202. As the dies 202 and 204 move from the intermediate position shown in FIG. 12 to the closed position shown in FIG. 13 the conical portions 222 and 224 of the dies engage the opposing ends of the sleeve blank 52B, deforming the ends radially inwards to generate the swaged ends 58 and 60 of the core sleeve 52. When the dies 202 and 204 are in the closed position shown in FIG. 13, the sleeve blank 52B is formed into the core sleeve 52. The dies 202 and 204 may then be opened and the formed sleeve 52 removed from the dies. FIG. 14 is a perspective view showing the core sleeve 52 after being removed from the die assembly 200. The above noted method for fabricating the core sleeve 52 is merely one example of a suitable fabrication method. In alternate embodiments, any other suitable methods may be used to form the sleeve including, for example, machining, casting, spin casting, forging, molding or any other suitable shaping method.

Figure 15:
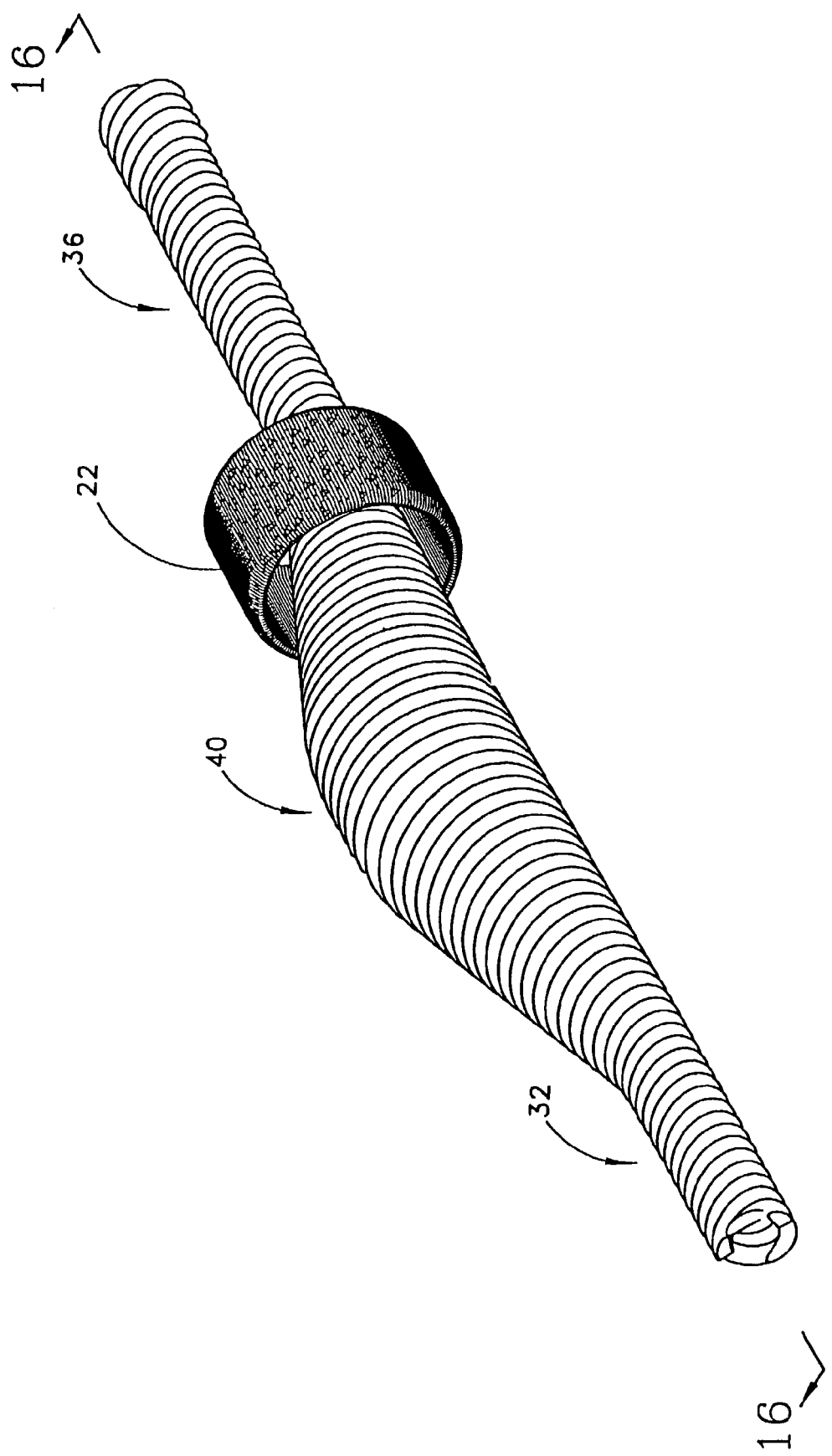
FIG. 15 is a partial perspective view of the drive shaft of the invention shown in FIG. 3, the eccentric tissue removal section being shown in a disassembled state with the abrasive sleeve or crown shown displaced from its installed position.

The abrasive sleeve 22 may be installed on the enlarged diameter section 34 of the drive shaft generally as described below and with particular reference to FIGS. 15-19. The sleeve 22 is placed over the drive shaft 14 preferably by moving the sleeve over the distal end of the drive shaft towards the enlarged diameter section 34. FIG. 15 is a perspective view of the drive shaft 14 and sleeve 22 showing the abrasive sleeve 22 on the drive shaft 14 but before assembly with the drive shaft. A cross-sectional view of this position is shown in FIG. 16. As seen in FIG. 16, the diameters 52E of the openings of the sleeve 22 at its swaged ends 58 and 60 are smaller than the maximum outer diameter of the enlarged diameter section 34 of the drive shaft 14 when the drive shaft is in an initial or unstretched state as shown in FIG. 16. In order to move the abrasive sleeve 22 over the enlarged diameter section 34, the enlarged diameter section may be stretched within the limits of the elastic deformation (resiliently stretched) by any suitable means such that in the stretched state the maximum outer diameter of this section is less than the diameters of the openings at swaged ends of the sleeve 22. By way of example, one method for resiliently stretching the enlarged diameter section may be by applying axial forces on the drive shaft as indicated by opposing arrows F in FIG. 17. The axial forces place the enlarged diameter section 34' in tension. Under this tension, the enlarged diameter section thus stretches resiliently in the axial direction. FIG. 17 shows the enlarged diameter section in the stretched condition. The enlarged diameter section is stretched sufficiently so that its maximum outer diameter is somewhat smaller than the diameters of the openings of the abrasive sleeve 22, yet preferably without yielding or permanent deformation resulting in any significant residual deformation in the enlarged diameter section. The axial forces on the drive shaft may be applied by any suitable means. With the enlarged diameter section maintained in this stretched state, the sleeve 22 is moved (in the direction indicated by arrow M in FIG. 17) over the enlarged diameter section 34' until the sleeve reaches the appropriate longitudinal position around the intermediate portion of the drive shaft. In this position shown in FIG. 18 the sleeve 22 is located substantially around the stretched intermediate portion of the enlarged diameter section. After the sleeve 22 is placed in its correct longitudinal location shown in FIG. 18, the axial forces on the drive shaft may be removed allowing the enlarged diameter section 34 to return to its initial or unstretched condition. The sleeve 22 is seated around the intermediate portion 40 of the enlarged diameter section as shown in FIG. 19. The wire turns 400 of the intermediate portion 40 are within the annular recess of the sleeve 22. The wire turns 380 and 420 of the proximal and distal conical sections engage the "turned in" lips 60 and 61 at the opposing ends of the sleeve at various locations around the circumference of the sleeve. This locks the sleeve 22 on the enlarged diameter section 34, thereby preventing the sleeve from moving axially along the shaft during operation of the rotational angioplasty device. As can be seen in FIG. 19. the abrasive layer located over the ends of the lips 59 and 61 of the sleeve 22 may be in contact or may be out of contact with the wire turns of the enlarged diameter section of the drive shaft. The wire turns of the intermediate portion 40 of the enlarged diameter section contact the inner surface 64 of the abrasive sleeve 22, and may be biased generally against the inner surface of the sleeve. This bias between the wire turns and the sleeve generates a friction force which further holds the sleeve on the enlarged diameter section and helps prevent the sleeve from rotating about the drive shaft. FIG. 19 also shows that in the preferred embodiment no abrasive is located on the inner surface of the abrasive sleeve 22.

FIGS. 20-23 are cross-sectional views similar to those shown in FIGS. 16-19. FIG. 20-23 show the drive shaft 14 and the sleeve 22 in four different conditions in accordance with a modified method for installing the sleeve on the drive shaft. In FIG. 20 the sleeve 22 is on the drive shaft in a position substantially similar to that shown in FIG. 16. In this modified method, a layer of adhesive 72 is deposited over the wire turns of the intermediate portion 40 of the enlarged diameter section. The adhesive 72 may be an epoxy adhesive or any other suitable type of adhesive. The layer of adhesive 72 is deposited around the exterior of the intermediate portion 40 by any suitable means such as touching wire turns with the epoxy adhesive or depositing a small drop or drops of adhesive on the intermediate portion area. In one embodiment as shown in FIG. 20, the layer of adhesive 72 is deposited on the intermediate portion 40 when the enlarged diameter section is in its initial or unstretched condition. As shown in FIGS. 20-23, after deposition of the adhesive 72 on the wire turns of the intermediate portion 40, the installation of the sleeve 22 on the enlarged diameter section 34 of the drive shaft proceeds in a manner substantially similar to that previously described. As seen in FIG. 21, the enlarged diameter section is stretched by applying opposing axial forces (in the direction indicated by arrows F) on the drive shaft. The maximum diameter of the stretched enlarged diameter section 34' becomes less than the diameter of the openings of the abrasive sleeve 22. Accordingly, the sleeve 22 may be moved in the direction indicated by arrow M over the stretched enlarged diameter section 34' until the sleeve reaches position shown in FIG. 22. The stretched enlarged diameter section 34 is then allowed to return to its unstretched or initial condition 34 (see FIG. 23), which places the intermediate portion 40 inside the annular recess in the sleeve 22. The adhesive 72 is located between the inner surface of the sleeve and the outer surface of the intermediate portion 40 of the enlarged diameter section 34 of the drive shaft. Authors of this invention successfully utilized epoxy adhesive EPO-TEK 301-2 for bonding abrasive sleeve or crown to the wire turns of the drive shaft. This epoxy adhesive is commercially available from Epoxy Technology Inc., Billerica, Mass. In the preferred method of the invention the epoxy adhesive EPO-TEK 301-2 is cured by placing the drive shaft for about 2 hours into an oven at 80° C. Alternatively epoxy adhesive EPO-TEK 301-2 may be cured at room temperature (18° C.-22° C.) for about 48 hours. A number of other adhesives may be utilized as well for bonding abrasive sleeve or crown to the drive shaft.

FIGS. 24-27 show another group of sectional views, similar to those in FIGS. 16-19 and 20-23, showing the drive shaft 14 and sleeve 22 in another four conditions in accordance with another modified method for installing the sleeve on the shaft. FIG. 24 shows the sleeve 22 around the drive shaft 14 in a position away from intermediate portion 40 of the enlarged diameter section 34 of the drive shaft. Prior to being placed in this position, the inner surface of the sleeve 22 is provided with a layer of adhesive 72. The adhesive may be epoxy or any other suitable adhesive. The adhesive 72 is deposited by any suitable means on the inner surface of the sleeve 22. The adhesive 72 is preferably deposited on the inner surface of sleeve before the sleeve is placed over the drive shaft. From position shown in FIG. 24, installation of the sleeve 22 on the drive shaft proceeds generally as shown in FIGS. 20-23. As in the previously described cases, the enlarged diameter section 34 of the drive shaft is stretched by applying opposing axial forces on the drive shaft on opposite sides of the enlarged diameter section as indicated by arrows F in FIG. 25. The stretched enlarged diameter section 34' now has a maximum diameter which is smaller than the diameters the openings of the sleeve 22. Hence, the sleeve 22 may be moved in the direction indicated by arrow M in FIG. 25 over the stretched enlarged diameter section 34'. The sleeve 22 is moved in direction M until the sleeve is placed around the intermediate portion of the stretched section 34' (see FIG. 26). The stretched enlarged diameter section 34' is then relaxed to return the section to the unstretched condition. This condition is shown in FIG. 27. In the unstretched condition, the wire turns of the intermediate portion 40 are nested into the annular recess of the sleeve 22 and thus are in contact with the adhesive layer 72 within the sleeve. This provides a bond between the sleeve 22 and the intermediate portion 40 securing the sleeve onto the enlarged diameter section 34 of the drive shaft.

Figure 28:
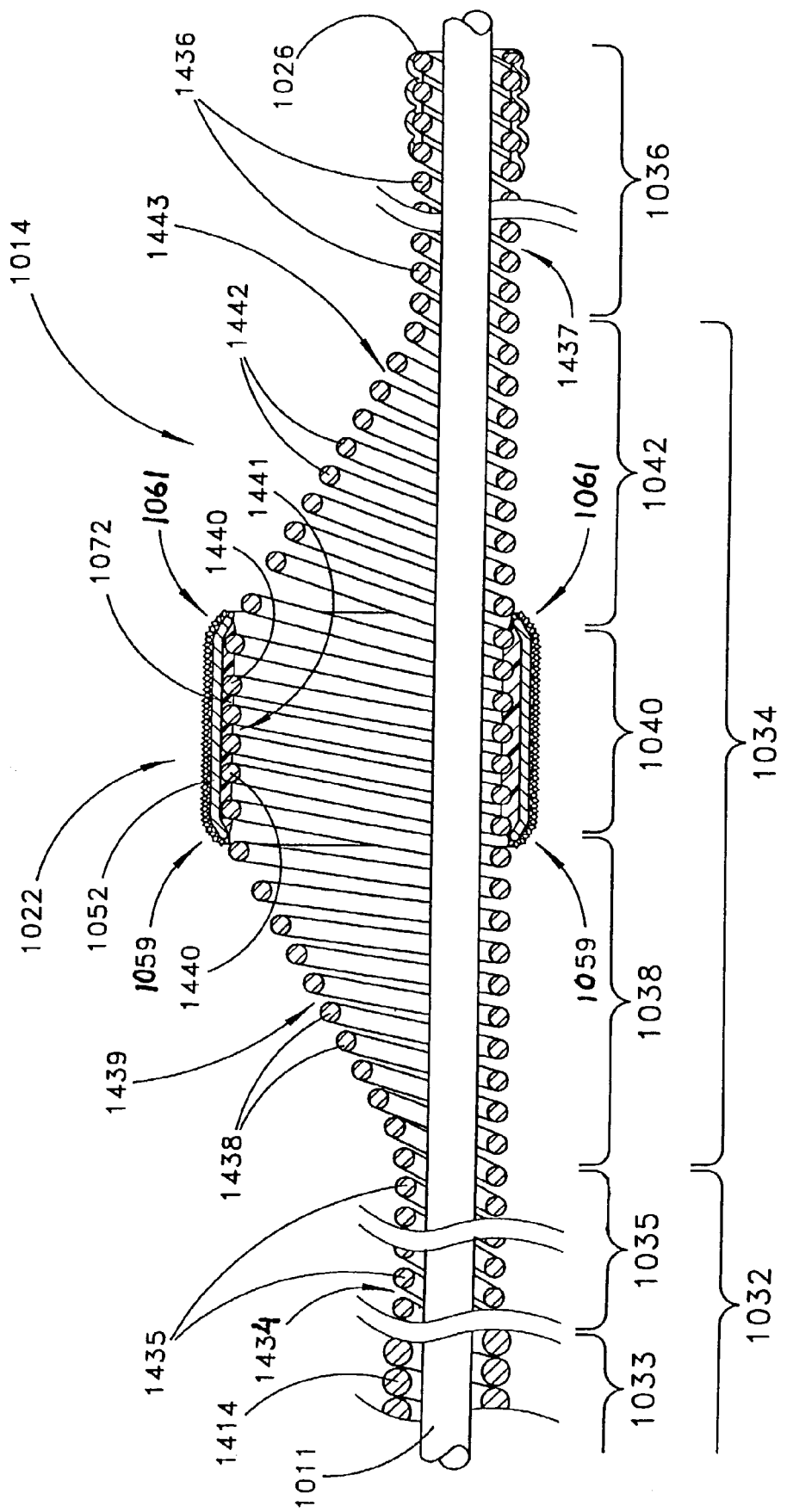
FIG. 28 is a partial cross-sectional view of a drive shaft of a rotational angioplasty device in accordance with another embodiment of the present invention.

Referring now to FIG. 28 there is shown in partial cross-sectional view a drive shaft 1014 of a rotational angioplasty device in accordance with a modified embodiment of the present invention. Except as otherwise noted below, the drive shaft 1014 is substantially similar to the drive shaft 14 described previously and shown in FIGS. 1A-1B, FIGS. 3-4 and FIGS. 20-27. Similar features of the drive shaft 1014 and the drive shaft 14 are similarly numbered. The drive shaft 1014 thus also includes an elongated proximal section 1032, an enlarged diameter section 1034, and an elongated distal section 1036. The enlarged diameter section 1034 comprises a proximal (conical or substantially conical) portion 1038, an intermediate portion 1040, and a distal (conical or substantially conical) portion 1042. The intermediate portion 1040 of the enlarged diameter section of the drive shaft may be very short and, if needed, may be simply formed by one or more wire turns located between the conical proximal portion 1038 and the conical distal portion 1042 of the enlarged diameter section 1034 of the drive shaft. In the assembled rotational angioplasty device, the elongated proximal section 1032 of the drive shaft 1014 is operatively connected to the prime mover (gas turbine) and extends distally to the enlarged diameter section 1034. As seen in FIG. 28, some wire turns 1435, 1438, 1440, 1442 and 1436 of the drive shaft 1014 have a smaller cross-section than the rest of the wire turns 1414 which make up the drive shaft. In particular, the elongated proximal section 1032 of the drive shaft includes a proximal portion 1033 made up of wire turns 1414 and a distal portion 1035 made up of wire turns 1435. As seen in FIG. 28 the wire turns 1435 making up the distal portion 1035 have smaller cross-section than the wire turns 1414 of the proximal portion 1033. It should be understood that the term "smaller cross-section wire turn(s)" as used herein implies that the wire of which a wire turns are made has a smaller cross-section than wire of which some other wire turns are made. It also should be understood that the wire out of which the "smaller cross-section wire turn(s)" are made may be the same wire which makes up the "larger cross-section wire turn(s)". Differences in the cross-section of the wire making up smaller or larger cross-section wire turns may be simply a result of etching some wire turns and not etching the others.

Wire turns 1435 of the distal portion 1035 of the elongated proximal section 1032 of the drive shaft are located consecutively between the proximal portion 1033 and the enlarged diameter section 1034. As shown in FIG. 28 consecutive or adjacent wire turns 1435 of the distal portion 1035 are separated from each other by gap(s) 1436. The wire turns 1414 of the proximal portion 1033 shown in FIG. 28 have substantially the same outer diameter as the other wire turns of the drive shaft located proximally to the distal portion 1035 of the elongated proximal section 1032 of the drive shaft. These slightly larger diameter wire turns make up the majority of the wire turns of the elongated proximal section 1032 of the drive shaft 1014. The enlarged diameter section 1034 of the drive shaft 1014 is similar to the enlarged diameter section 34 described previously and shown in FIGS. 3 and 4. The enlarged diameter section 1034 is asymmetric or eccentric relative to the general axis of rotation of the drive shaft. In FIG. 28 this general axis of rotation of the drive shaft is formed by a guide wire 1011. The enlarged diameter section 1034 is comprised of proximal and distal conical portions 1038 and 1042 and intermediate portion 1040 which is located in between conical portions. The enlarged diameter section 1034 comprises wire turns 1438, 1440 and 1442 having reduced cross-section relative to the cross-section of the wire turns 1414 making up the proximal portion 1033 of the elongated proximal section 1032 of the drive shaft 1014. Consecutive or adjacent wire turns 1438, 1440, 1442 respectively in the proximal, intermediate, and distal portions 1038, 1040 and 1042 of the enlarged diameter section are separated by corresponding gaps 1439, 1441 and 1443 as shown in FIG. 28. The elongated distal section 1036 of the drive shaft is made up of wire turns 1436 with the reduced cross-section. Consecutive or adjacent wire turns 1436 are separated by gaps 1437. The reduced cross-section wire turns 1435, 1438, 1440, 1442 and 1436 of drive shaft 1014 may be formed by etching the wire turns using a suitable solution for removing material from outer surfaces of the wire turns. By way of example, prior to placing an abrasive sleeve or crown 1022 on the drive shaft a portion of the drive shaft from distal end 1026 to the proximal portion 1033 of the elongated proximal section 1032 may be immersed into an etching solution. In one embodiment of this invention a solution of sulfuric acid ($H_2SO_4$) was used as the etching agent. Electrochemical etching in a solution of sulfuric acid with specific gravity of about 1,58 grams per cubic centimeter was successfully utilized. The portion of the drive shaft with reduced cross-section of wire turn remains immersed into the etching solution until a sufficient amount of material is removed from each of the immersed wire turns such that the wire turns have a desired reduced cross-section. Preferably, all of the immersed wire turns have a similar amount of material removed from their outer surfaces resulting in the wire turns 1435, 1438, 1440, 1442 and 1436 having substantially similar reduced cross-sections compared to the cross section of the wire, turns 1414 which are not immersed in the etching solution. It should be noted, that in the preferred method of the invention, a TFE beading (Teflon thread) is introduced into a lumen of the drive shaft prior to immersing the drive shaft in the etching solution. Such an introduction of the Teflon thread or beading into the lumen of the drive shaft prevents etching of wire turns from inside and therefore the diameter of the lumen of the drive shaft remains substantially unchanged. In FIG. 28 the cross-section of the reduced cross-section wire turns 1435, 1438, 1440, 1442 and 1436 is shown as being substantially round. It should be noted that the wire turns with reduced cross-section are shown in FIG. 28 as being substantially round only to simplify the drawing and that these reduced cross section wire turns usually are not perfectly round and that the individual cross-sectional shape of these wire turns may vary somewhat between individual wire turns. Removal of material from the cross-section of wire turns 1435, 1438, 1440, 1442 and 1436 provides a relatively small but well controlled reduction of the outer diameters of the corresponding etched sections and portions of the drive shaft relative to the rest of the drive shaft. In the preferred embodiment of the invention the outer diameters of the distal elongated section 1036 and of the distal portion 1035 are reduced by etching by about 35 microns (see FIG. 9B for more details). The distal etched portion 1035 has length of about 15 mm, but may be made shorter or longer, if so desired. The removal of material during etching allows to form or enhance the gaps 1434, 1439, 1441, 1443 and 1437 between respective consecutive wire turns 1435, 1438, 1440, 1442 and 1436 of the drive shaft. The reduced cross-section wire turns 1435, 1438, 1440, 1442, 1436 and the gaps 1434, 1439, 1441, 1443, 1437 between the respective consecutive wire turns provide the corresponding distal 1036 and enlarged diameter 1034 sections of the drive shaft as well as its distal portion 1035 of the elongated proximal portion 1032 with increased flexibility as compared to the similar sections or portions of the drive shaft 14. This etching and therefore increase in flexibility of only portion of the drive shaft represents one of the ways which allow to increase an amount of time during which the drive shaft 1014 of FIG. 28 may be rotated within a tortuous vessel over a small diameter guide wire without causing fatigue fracture of either the guide wire or the drive shaft itself.

Referring again to FIG. 28, an abrasive sleeve 1022 is mounted on the enlarged diameter section 1034 of the drive shaft 1014. The abrasive sleeve 1022 is substantially the same as the abrasive sleeve 22 described previously and shown in FIGS. 3-27.

Still referring to FIG. 28, the abrasive sleeve or crown 1022 is mounted on the intermediate portion 1040 of the enlarged diameter section 1034. The wire turns 1440 of the intermediate portion 1040 are located in the annular recess of the core sleeve 1052. An adhesive 1072 may be deposited on the wire turns 1440 of the intermediate portion 1040 or on the inner surface of the abrasive sleeve 1022 prior to mounting the sleeve on the drive shaft in order to bond the sleeve to the wire turns of the enlarged diameter section 1040 of the drive shaft. The abrasive sleeve 1022 may be mounted on the drive shaft using methods described before and shown in FIGS. 16-27.

Figure 29:
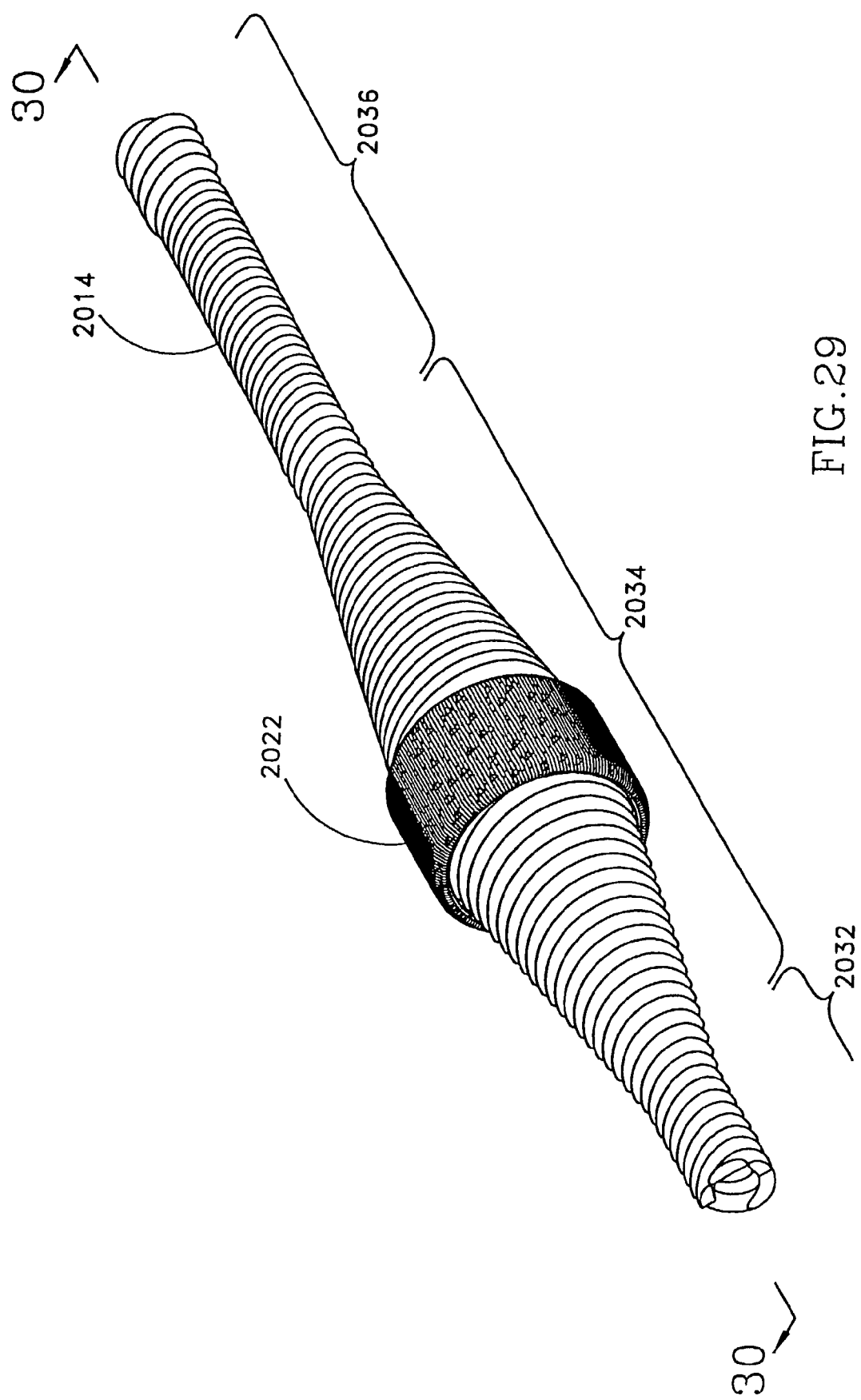
FIG. 29 is a partial perspective view of a portion of a drive shaft of the rotational angioplasty device where the abrasive sleeve or crown of the present invention is a part of a symmetric tissue removal section.

Referring now to FIG. 29, there is shown a partial perspective view of a drive shaft 2014 of a rotational angioplasty device in accordance with another embodiment of the present invention.

Figure 30:
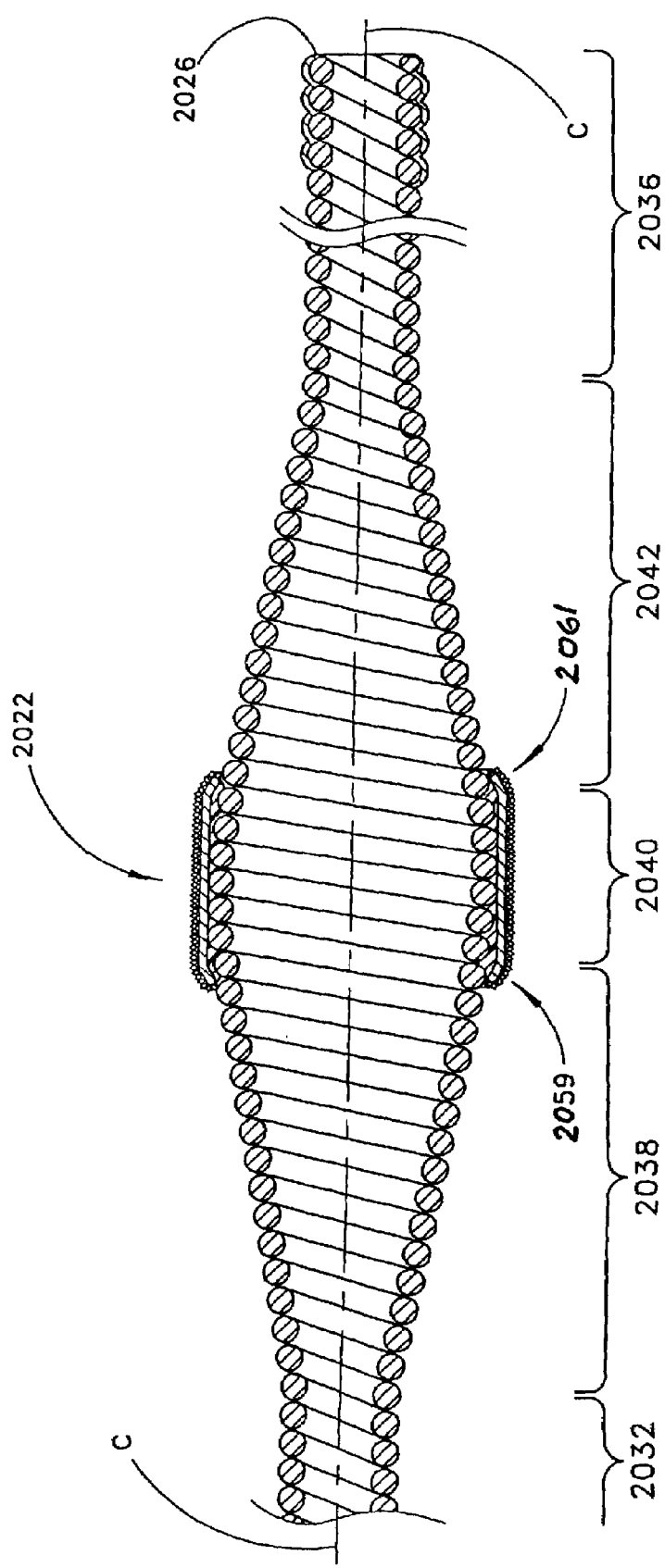
FIG. 30 is a cross-sectional view of the portion of the drive shaft and tissue removal section taken along line 30-30 in FIG. 29, the abrasive sleeve or crown of the present invention shown bonded to the drive shaft.
Figure 31:
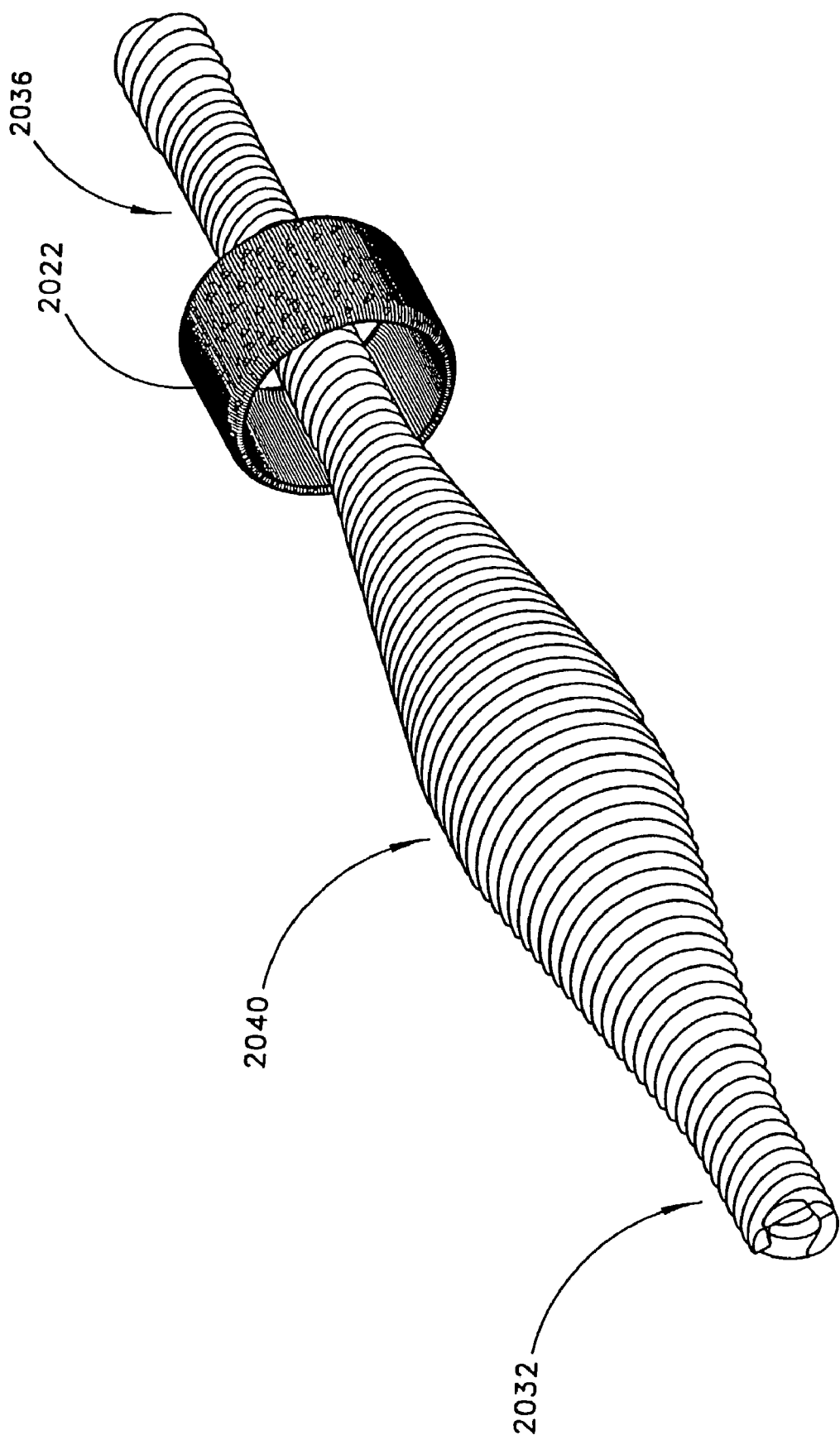
FIG. 31 is a partial perspective view of the portion of the drive shaft of the invention shown in FIG. 29, the symmetric tissue removal section being shown in disassembled state with the abrasive sleeve or crown shown displaced from its installed position.
Figure 32:
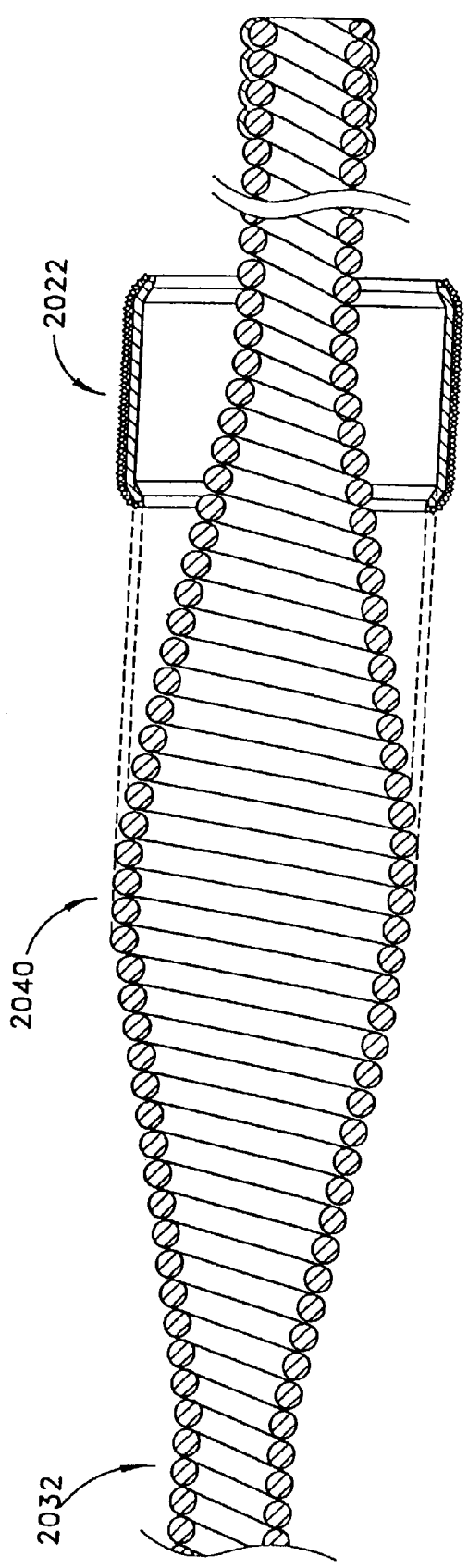
FIGS. 32-35 are showing the same method of assembly of a tissue removal section of the drive shaft as shown in FIGS. 16-19, except for the tissue removal section in FIGS. 32-35 being symmetric.
Figure 33:
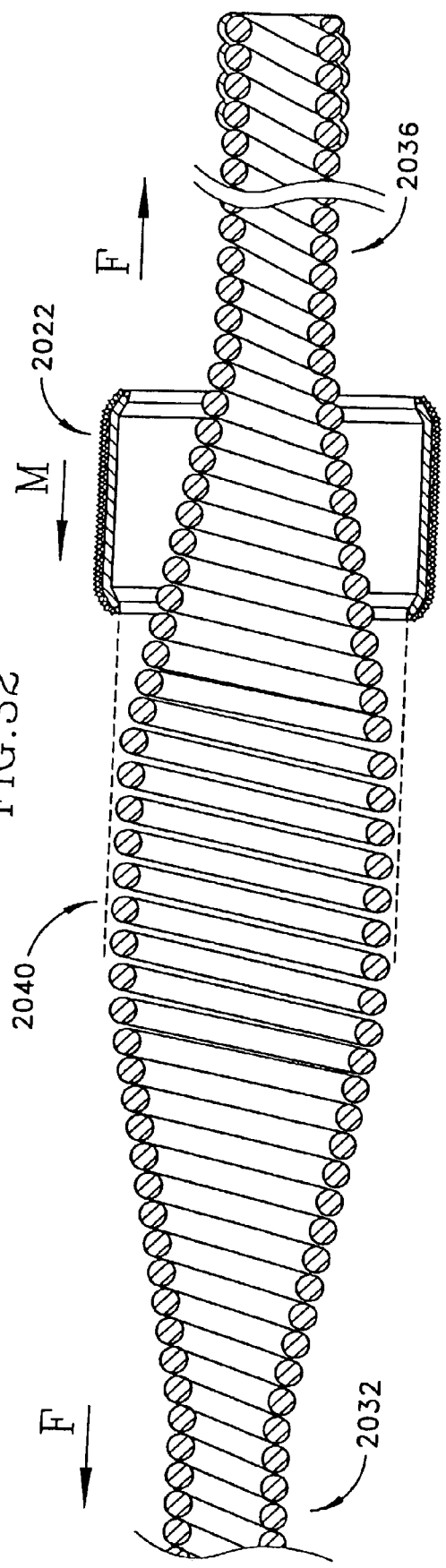
Figure 34:
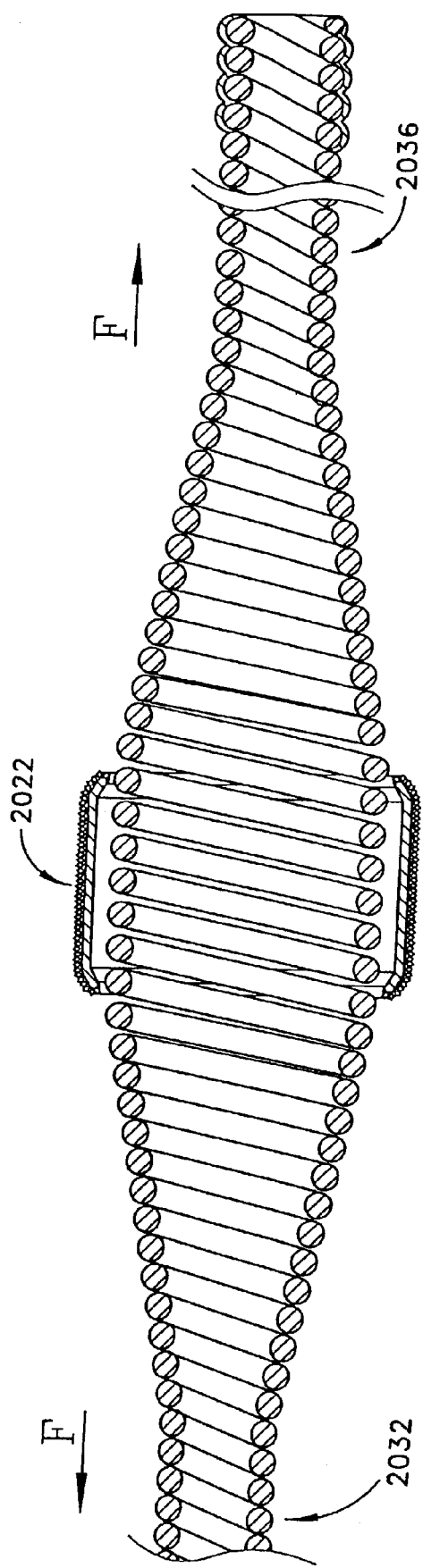
Figure 35:
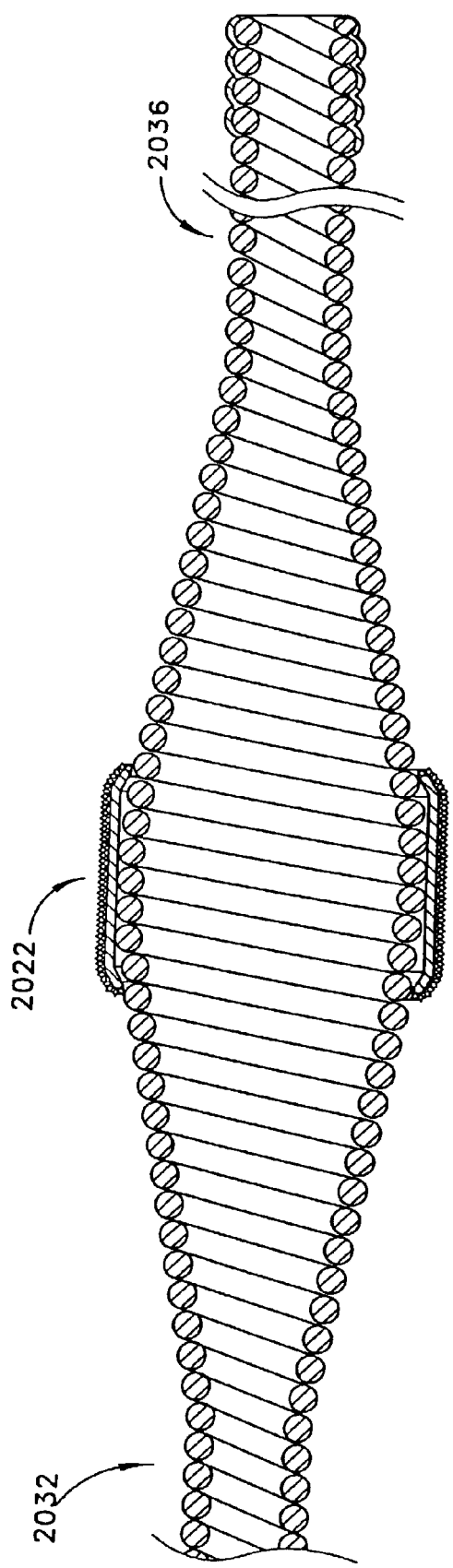
Figure 36:
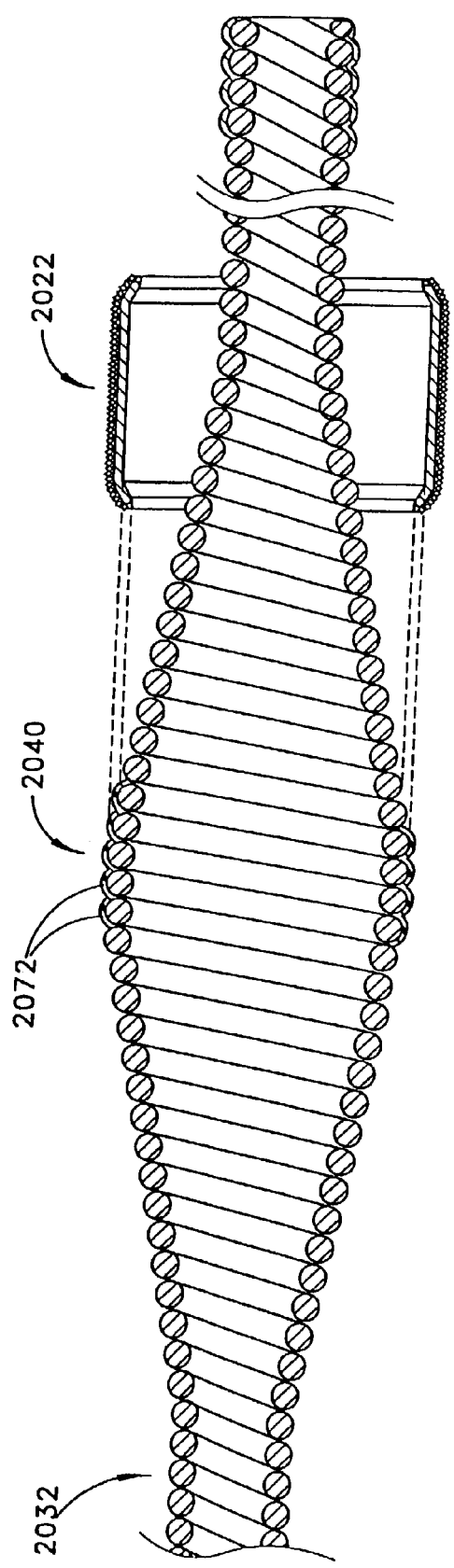
Figure 37:
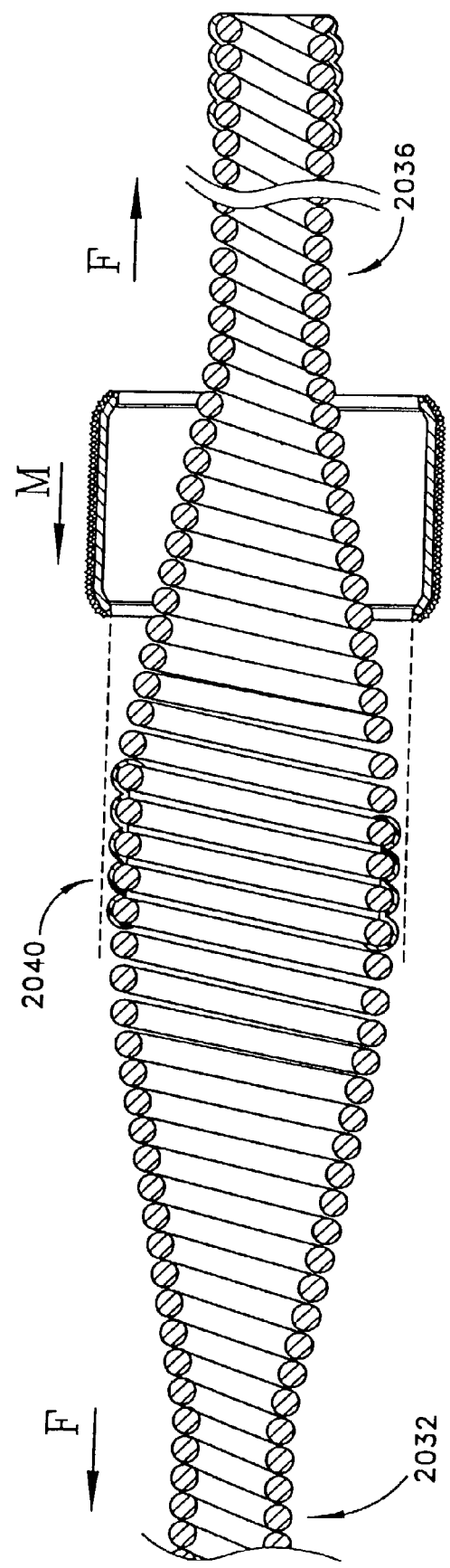
Figure 40:
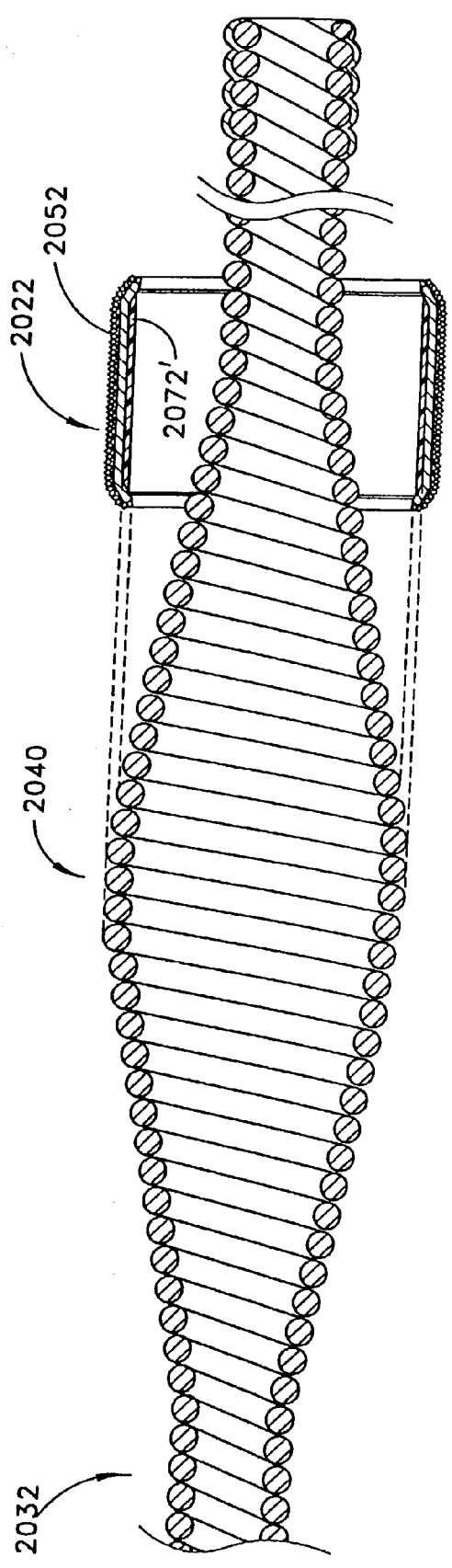
FIGS. 40-43 are showing the same method of assembly of a tissue removal section of the drive shaft as shown in FIGS. 24-27, except for the tissue removal section in FIGS. 40-43 being symmetric.
Figure 41:
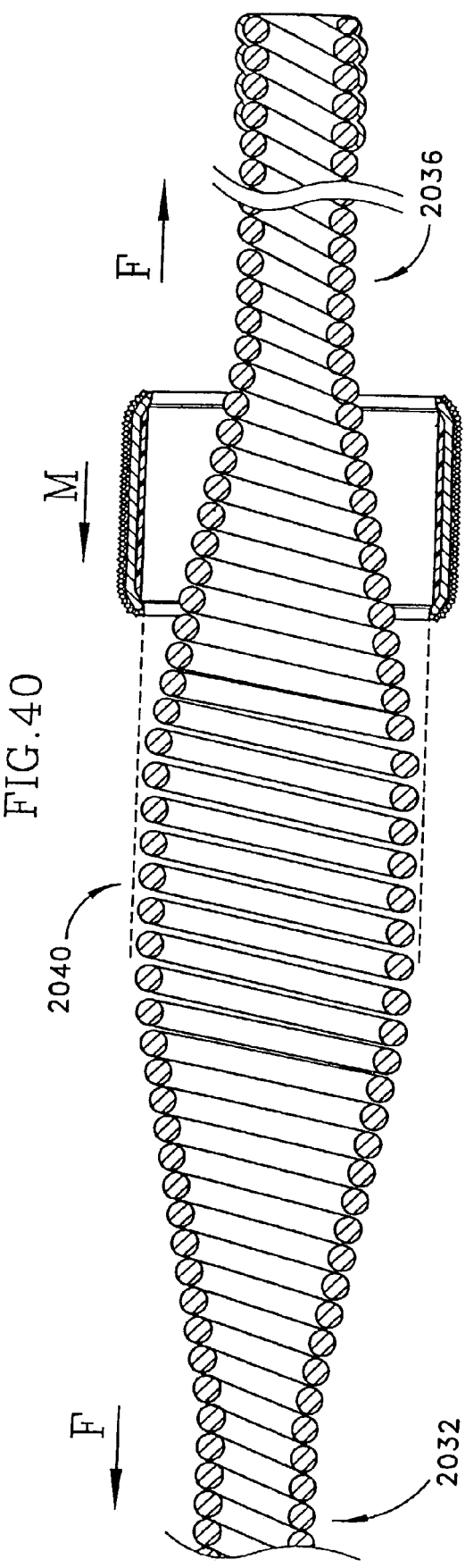
Figure 42:
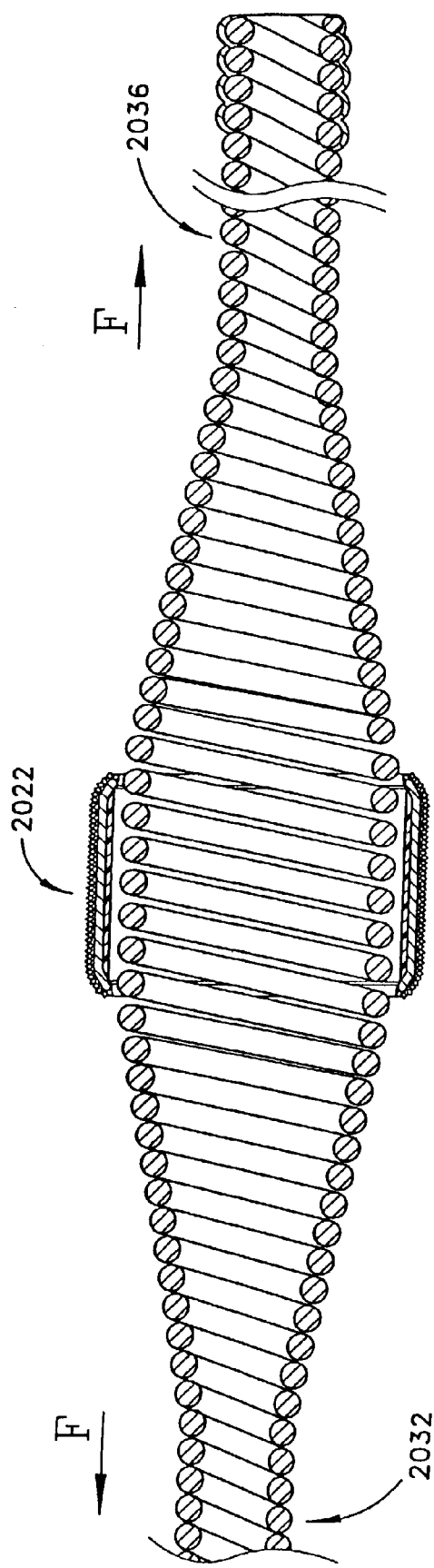
Figure 43:
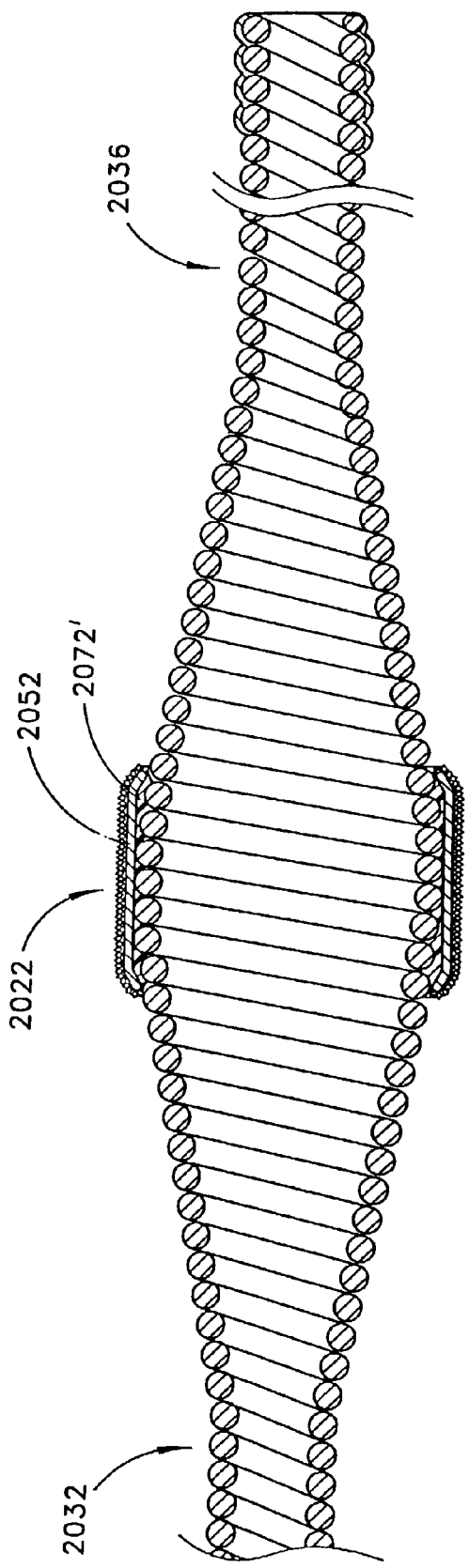

FIG. 30 shows a cross-sectional view of a portion of the drive shaft 2014 taken along line 30-30 in FIG. 29. Similar features of the drive shaft 2014 and the drive shaft 14 are similarly numbered.

Drive shaft 2014 has an abrasive sleeve or crown 2022 which is substantially identical or similar to the abrasive sleeve or crown 22 described before and shown in FIGS. 1A-1B and in FIGS. 3-27. The abrasive crown shown in FIGS. 1A-1B and in FIGS. 3-27 is shown mounted on the eccentric enlarged diameter segment of the drive shaft while the abrasive sleeve or crown 2022 shown in FIGS. 29-43 is mounted on an enlarged diameter segment 2034 which is symmetric with respect to a longitudinal or rotational axis C-C of the drive shaft.

The wire turns of the proximal conical portion 2038 of the enlarged diameter section increase distally in diameter at a substantially constant rate, and the distal conical portion 2042 has wire turns which decrease distally in diameter at a substantially constant rate. As seen in FIG. 30, the intermediate portion 2040 has consecutive wire turns which may be substantially of the same outer diameter.

Figure 44:
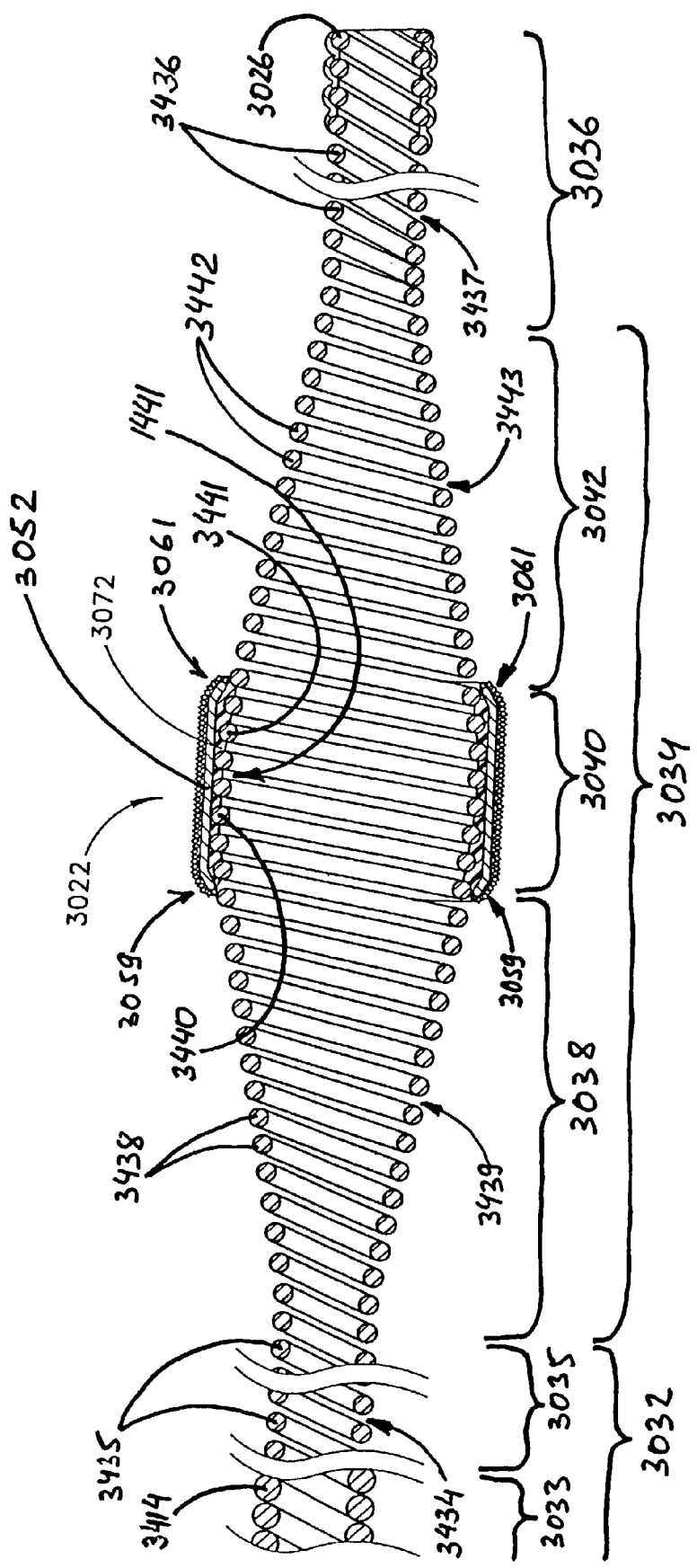
FIG. 44 is a partial cross-sectional view of a drive shaft of a rotational angioplasty device in accordance with yet another embodiment of the present invention.
Figure 45:
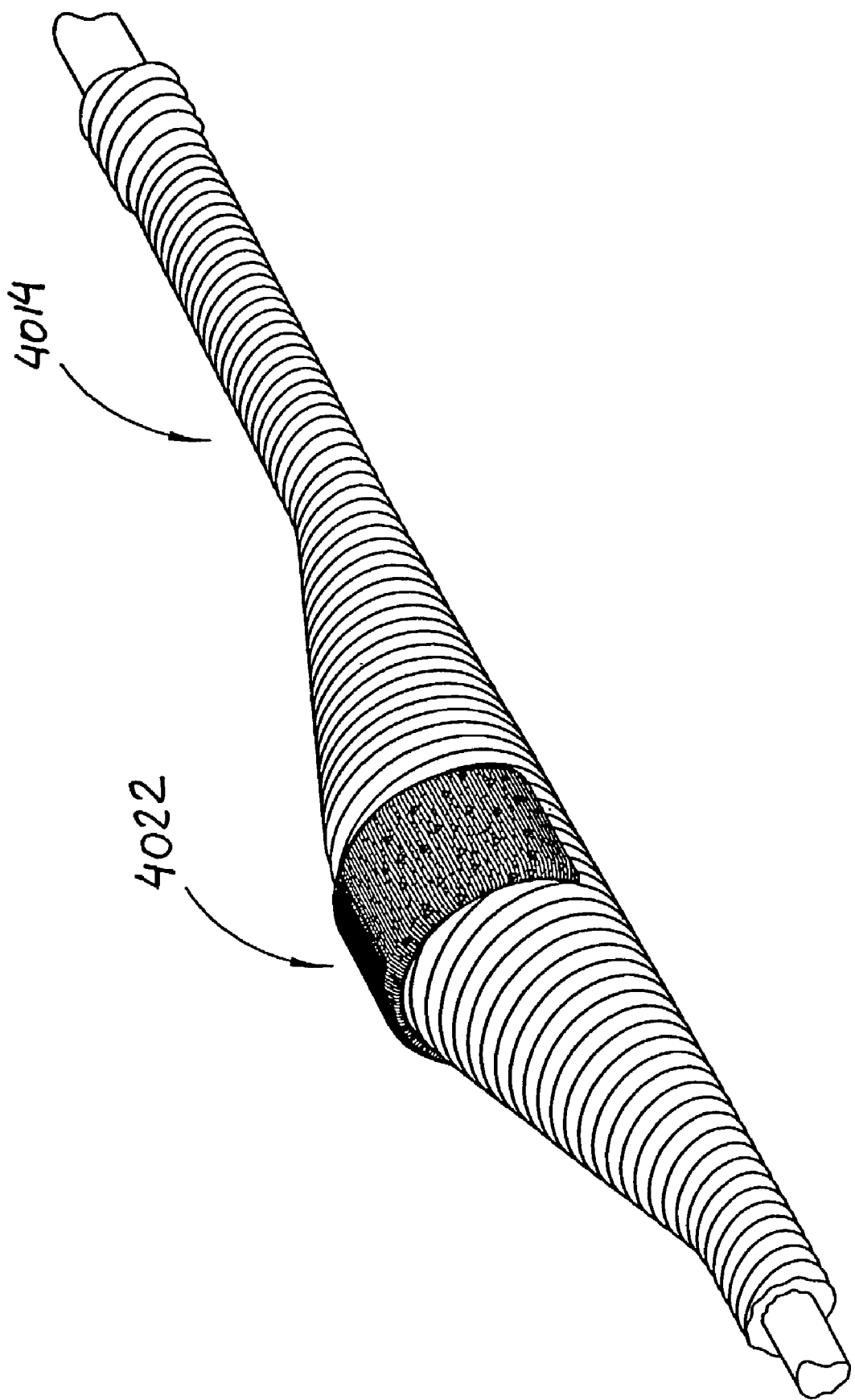
FIG. 45 is a perspective view of a modified abrasive crown of the invention mounted on the eccentric enlarged diameter segment of the drive shaft.
Figure 46:
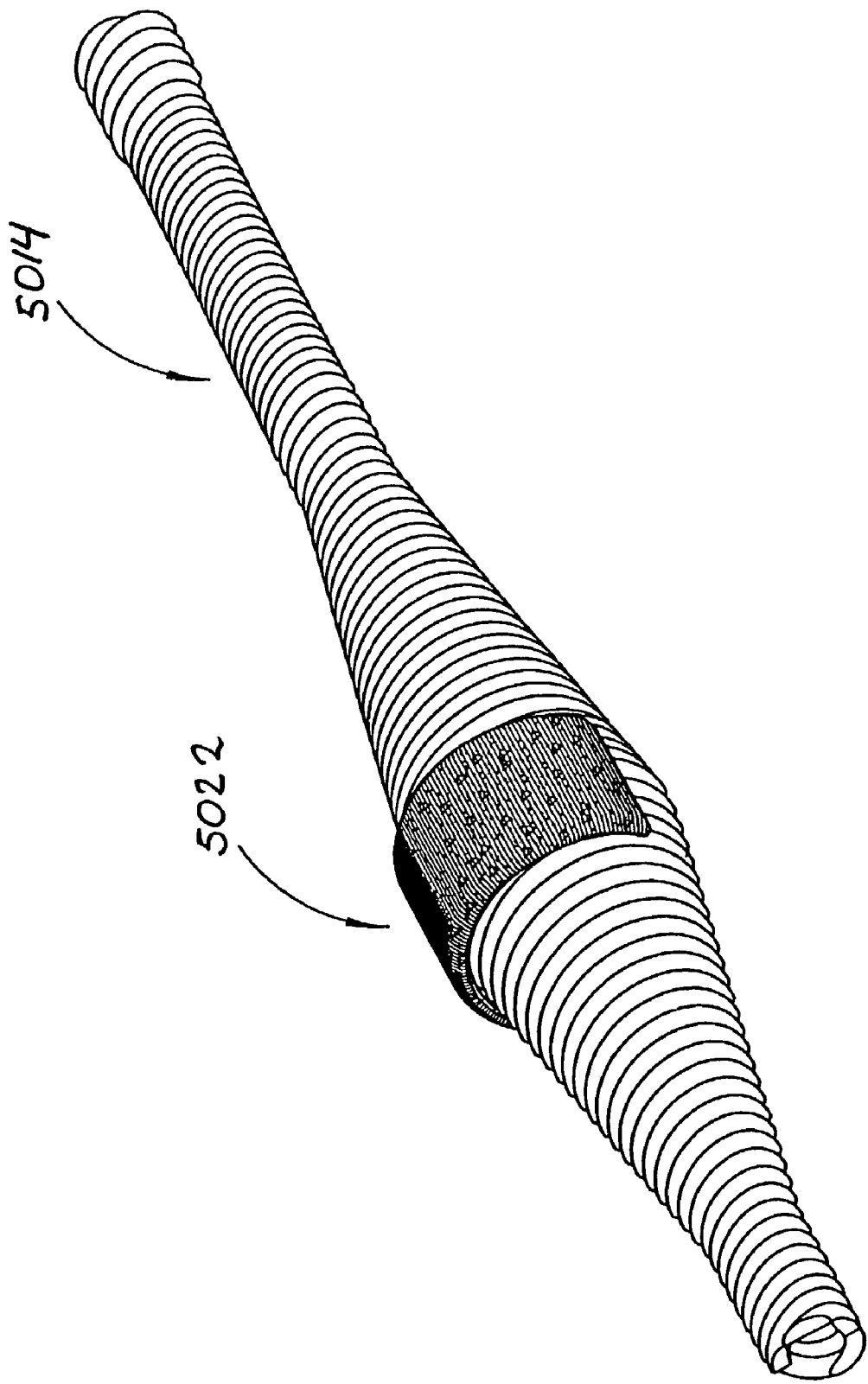
FIG. 46 is a perspective view showing a modified abrasive crown similar to the crown shown in FIG. 44, but mounted on the symmetric enlarged diameter section of the drive shaft.

FIGS. 31-43 show methods which may be used for mounting the abrasive sleeve or crown 2022 on the enlarged diameter section of the drive shaft. Both the basic method for mounting the abrasive sleeve and its modifications are the same as shown in FIGS. 15-27 and involve resiliently stretching the enlarged diameter section 2034 so that in the stretched state the maximum outer diameter of this section is smaller than the diameter of the openings at the swaged ends of the sleeve 2022. Referring now to FIG. 44, there is shown a partial cross-section view of a drive shaft 3014 of a rotational angioplasty device in accordance with yet another modified embodiment of the present invention. Drive shaft 3014 is substantially similar to drive shaft 2014 described previously and shown in FIGS. 29 and 30 except as otherwise noted below. Similar features of the drive shaft 3014 and the drive shaft 2014 are similarly numbered. Drive shaft 3014 thus also includes an elongated proximal section 3032, a symmetric enlarged diameter section 3034, and an elongated distal section 3036.

As seen in FIG. 44 some wire turns 3435, 3438, 3440 and 3436 of the drive shaft 3014 have a smaller cross-section then the rest of the wire turns 3414 making up the drive shaft. The elongated proximal section 3032 of the drive shaft includes a proximal portion 3033 made up of wire turns 3414 and a distal portion 3035 made up of the smaller cross-section wire turns 3435. Consecutive wires turns 3435 of the distal portion 3035 are shown as separated by gaps 3436. Wire turns 3414 make up a majority of the wire turns of the elongated proximal section. The symmetric enlarged diameter section 3034 of the drive shaft 3014 is similar to the symmetric enlarged diameter section 2034 described previously and shown in FIGS. 29-30. The symmetric enlarged diameter section 3034 is comprised of proximal and distal conical sections 3038, 3042 with intermediate section 3040 located in between. The enlarged diameter section 3034 comprises wire turns 3438, 3440 and 3442 of reduced cross-section relative to the cross-section of the wire turns 3414 making up the proximal portion 3033 of the drive shaft 3014. Consecutive wire turns 3438, 3440 and 3442 in the proximal, intermediate, and distal portions 3038, 3040 and 3042 of the enlarged diameter section 3034 are separated by corresponding gaps 3439, 3441 and 3443 shown in FIG. 44. The elongated distal section 3036 of the drive shaft 3014 is made up of wire turns 3436 with the reduced cross-section. Consecutive wire turns 3436 are also shown as separated by gaps 3437. The reduced cross-section wire turns 3435, 3438, 3440, 3442 and 3436 of the drive shaft 3014 may be formed by etching the wire turns using a suitable solution for removing material from the wire turns. The method for etching a portion of the symmetric drive shaft 3014 is the same as the method described for etching asymmetric or eccentric drive shaft 1014 shown in FIG. 28. Still referring to FIG. 44, an abrasive sleeve 3022 is mounted on the enlarged diameter section 3034. The abrasive sleeve or crown 3022 is substantially the same as sleeve 22 described previously and shown in FIGS. 3-43. The intermediate portion 3040 is located inside the sleeve 3022 thereby fixing the sleeve 3022 on the drive shaft. An adhesive layer 3072 may be provided between sleeve 3022 and outer surface of the wire turns of the intermediate portion 3040 to bond the sleeve to the intermediate portion.

FIGS. 47 and 48 illustrate a very important feature of this invention which is common to all embodiments of the invention. FIG. 48 shows that loose fixation of the abrasive sleeve 22 on the enlarged diameter section of the drive shaft will cause wire turns of the rotating drive shaft to act as threads of a bolt and move the sleeve or crown longitudinally proximally with respect to the drive shaft, thereby preventing the sleeve from becoming "lost" in e.g. a coronary (heart) vessel. It is a feature of the present invention that both the direction of the wire turns of the drive shaft and the direction of the rotation of the drive shaft are such that rotating drive shaft has a tendency to move the abrasive sleeve or crown proximally with respect to the drive shaft. Bonding of the abrasive sleeve or crown to the wire turn of the enlarged diameter section of the drive shaft with adhesive prevents rotational movement of the drive shaft with respect to the crown, thereby preventing longitudinal movement of the sleeve or crown with respect to the drive shaft.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A rotational angioplasty device comprising:

a flexible, elongated drive shaft rotatable about an axis of rotation of the drive shaft, the drive shaft comprising one or more helically wound wires and having an enlarged diameter section capable of being stretched, the enlarged diameter section having a stretched maximum diameter and an unstretched maximum diameter, the enlarged diameter section having a substantially conical proximal portion comprising wire turns, a substantially conical distal portion comprising wire turns and an intermediate portion, the portion formed at the junction between the conical and distal proximal portions, wherein the intermediate portion comprises the stretched and unstretched maximum diameter of the enlarged diameter section of the drive shaft;

a substantially circular and hollow prefabricated abrasive crown installed over at least the intermediate portion of the enlarged diameter section of the drive shaft, the abrasive crown comprising:

a substantially flat section, the flat section comprising an outer surface and an inner surface terminating in inwardly tapered circumferential lips having a diameter that is less than the maximum unstretched diameter of the enlarged diameter section and greater than the stretched maximum diameter of the enlarged diameter section, the lips further comprising an inner surface and an outer surface; and abrasive material on the outer surface of the substantially flat section of the abrasive crown, the abrasive material separated from the wire turns of the enlarged diameter section by the abrasive crown, wherein the unstretched wire turns of the substantially conical proximal section and distal proximal section engage the inner surface of the circumferential lips of the installed abrasive crown, and wherein the wire turns of the enlarged diameter section are bonded to and biased against the inner surface of the flat section and biased against the inner surface of the circumferential lips of the installed abrasive crown.

2. The rotational angioplasty device according to claim 1, wherein the abrasive crown on the enlarged diameter section defines a tissue removal section of the device.

3. The rotational angioplasty device according to claim 1, wherein the abrasive crown has swaged ends for holding the abrasive crown around the enlarged diameter section of the drive shaft.

4. The rotational angioplasty device according to claim 1, wherein the abrasive crown circumferentially contacts wire turns of the enlarged diameter section such that the abrasive crown forms a tight fit around the enlarged diameter section of the drive shaft.

5. The rotational angioplasty device according to claim 1, wherein the crown is made of metal, composite material, elastomeric material, or plastic.

6. The rotational angioplasty device according to claim 1, wherein the sleeve has a pair of swaged ends.

7. The rotational angioplasty device according to claim 1, wherein the crown has swaged ends defining an annular recess in the crown, and wherein wire turns of the enlarged diameter section are captured in the annular recess for holding the abrasive crown on the enlarged diameter section of the drive shaft.

8. The rotational angioplasty device according to claim 1, wherein wire turns of the enlarged diameter section are biased radially outwards against the crown, and at least one of the wire turns engages a circumferential lip of the crown for holding the abrasive crown on the enlarged diameter section of the drive shaft.

9. The rotational angioplasty device according to claim 1, wherein the abrasive layer is disposed over the outer surface of at least one circumferential lip.

10. The rotational angioplasty device according to claim 1, wherein the abrasive layer is disposed over the outer surface of at least the lip that is located at a distal end of the crown.

11. A rotational angioplasty device driveshaft comprising:
a flexible, elongated drive shaft rotatable about an axis of rotation of the drive shaft, the drive shaft comprising one or more helically wound wires and having an eccentric enlarged diameter section capable of being stretched, the eccentric enlarged diameter section having a stretched maximum diameter and an unstretched maximum diameter, the eccentric enlarged diameter section having a substantially conical proximal portion comprising wire turns, a substantially conical distal portion comprising wire turns and an intermediate portion, the portion formed at the junction between the conical and distal proximal portions, wherein the intermediate portion comprises the stretched and unstretched maximum diameter of the enlarged diameter section of the drive shaft;
a substantially circular and hollow prefabricated abrasive crown installed over at least the intermediate portion of the eccentric enlarged diameter section of the drive shaft, the abrasive crown comprising:
a substantially flat section, the flat section comprising an outer surface and an inner surface terminating in inwardly tapered circumferential lips having a diameter that is less than the maximum unstretched diameter of the eccentric enlarged diameter section and greater than the stretched maximum diameter of the eccentric enlarged diameter section, the lips further comprising an inner surface and an outer surface; and
abrasive material on the outer surface of the substantially flat section of the abrasive crown comprising a tissue removing surface which defines a tissue removing section of the drive shaft, the abrasive material separated from the wire turns of the eccentric enlarged diameter section by the abrasive crown, wherein the unstretched wire turns of the substantially conical proximal section and distal proximal section engage the inner surface of the circumferential lips of the installed abrasive crown, and wherein the wire turns of the eccentric enlarged diameter section are bonded to and biased against the inner surface of the flat section and biased against the inner surface of the circumferential lips of the installed abrasive crown.

12. The rotational angioplasty device drive shaft according to claim 11, wherein the prefabricated crown is covering a number of wire turns of the eccentric enlarged diameter section, and wherein the crown is made of steel, brass, copper alloy, a high radio-opacity alloy, composite material, elastomeric material, or plastic.

13. The rotational angioplasty device drive shaft according to claim 12, wherein the radio-opacity alloy is platinum alloy, tantalum alloy, nickel alloy, or tungsten alloy.

14. The rotational angioplasty device drive shaft according to claim 11, wherein the prefabricated crown has a downturned circumferential lip at least at one end of the prefabricated crown.

15. The rotational angioplasty device drive shaft according to claim 11, wherein the prefabricated crown has a pair of downturned circumferential lips, one lip being located at each of a distal and proximal ends of the prefabricated crown.

16. The rotational angioplasty device drive shaft according to claim 11, wherein the prefabricated crown has swaged ends defining an annular recess in the prefabricated crown, and wherein wire turns of the enlarged diameter section of the drive shaft are captured in the annular recess for holding the prefabricated crown on the drive shaft.

17. The rotational angioplasty device drive shaft according to claim 11, wherein wire turns of the enlarged diameter section of the drive shaft are biased radially outwards against the prefabricated crown, and at least one of the wire turns engages a lip of the prefabricated crown for holding the prefabricated crown on the drive shaft.

18. The rotational angioplasty device drive shaft according to claim 11, wherein the prefabricated crown has a downturned circumferential lip located at least at one end of the prefabricated crown, and wherein the abrasive layer is disposed over an outer surface of the lip.

19. The rotational angioplasty device drive shaft according to claim 11, wherein the prefabricated crown has a pair of downturned circumferential lips, one lip being located at each of a distal and proximal ends of the prefabricated crown, and wherein the abrasive layer is disposed over an outer surface of both lips.

20. The rotational angioplasty device drive shaft according to claim 11, wherein the prefabricated crown has a circumferential lip turned inwards towards a longitudinal axis of the prefabricated crown, the lip being located at least at one end of the prefabricated crown, and wherein the abrasive layer is disposed over an outer surface of the lip.

21. The rotational angioplasty device drive shaft according to claim 11, wherein the prefabricated crown has a pair of circumferential lips turned inwards towards a longitudinal axis of the prefabricated crown, one lip being located at each of a distal end and a proximal end of the prefabricated crown, and wherein the abrasive layer is disposed over an outer surface of both lips.

* * * * *

UNITED STATES PATENT AND TRADEMARK OFFICE
CERTIFICATE OF CORRECTION

PATENT NO. : 7,507,245 B2 Page 1 of 1
APPLICATION NO. : 10/272164
DATED : March 24, 2009
INVENTOR(S) : Leonid Shturman et al.

It is certified that error appears in the above-identified patent and that said Letters Patent is hereby corrected as shown below:

Title page, should read as follows:

Related U.S. Application Data: Item

--(60) Provisional application No. 60/343,825, filed on Oct. 19, 2001.--

Signed and Sealed this

Fifth Day of May, 2009

JOHN DOLL
*Acting Director of the United States Patent and Trademark Office*